(12) United States Patent
Shults et al.

(10) Patent No.: US 7,875,293 B2
(45) Date of Patent: *Jan. 25, 2011

(54) BIOINTERFACE MEMBRANES INCORPORATING BIOACTIVE AGENTS

(75) Inventors: Mark Shults, Madison, WI (US); James H. Brauker, San Diego, CA (US); Victoria Carr-Brendel, Pleasanton, CA (US); Mark Tapsak, Orangeville, PA (US); Dubravka Markovic, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 749 days.

This patent is subject to a terminal disclaimer.

(21) Appl. No.: 10/842,716

(22) Filed: May 10, 2004

(65) Prior Publication Data

US 2005/0031689 A1    Feb. 10, 2005

Related U.S. Application Data

(63) Continuation-in-part of application No. 10/647,065, filed on Aug. 22, 2003, now Pat. No. 7,192,450.

(60) Provisional application No. 60/472,673, filed on May 21, 2003, provisional application No. 60/544,722, filed on Feb. 12, 2004.

(51) Int. Cl.
  *A61K 9/70*     (2006.01)
  *A61F 2/02*     (2006.01)
  *C12Q 1/54*     (2006.01)

(52) U.S. Cl. .............. 424/473; 424/424; 424/425; 424/486; 435/14; 623/23.76

(58) Field of Classification Search .......... None
See application file for complete search history.

(56) References Cited

U.S. PATENT DOCUMENTS

| | | |
|---|---|---|
| 3,775,182 A | 11/1973 | Patton et al. |
| 3,898,984 A | 8/1975 | Mandel et al. |
| 3,929,971 A | 12/1975 | Roy |
| 3,943,918 A | 3/1976 | Lewis |
| 3,957,651 A * | 5/1976 | Kesting ............ 210/490 |
| 3,964,974 A | 6/1976 | Banauch et al. |
| 3,966,580 A | 6/1976 | Janata et al. |
| 3,979,274 A | 9/1976 | Newman |
| 4,024,312 A | 5/1977 | Korpman |
| 4,040,908 A | 8/1977 | Clark, Jr. |
| 4,073,713 A | 2/1978 | Newman |
| 4,076,656 A | 2/1978 | White et al. |
| 4,172,770 A | 10/1979 | Semersky et al. |
| 4,197,840 A | 4/1980 | Beck et al. |
| 4,215,703 A | 8/1980 | Willson |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,260,725 A | 4/1981 | Keogh et al. |
| 4,353,888 A | 10/1982 | Sefton |
| 4,374,013 A | 2/1983 | Enfors |
| 4,388,166 A | 6/1983 | Suzuki et al. |
| 4,403,984 A | 9/1983 | Ash et al. |
| 4,415,666 A | 11/1983 | D'Orazio et al. |
| 4,418,148 A | 11/1983 | Oberhardt |
| 4,431,004 A | 2/1984 | Bessman et al. |
| 4,436,094 A | 3/1984 | Cerami |
| 4,442,841 A | 4/1984 | Uehara et al. |
| 4,477,314 A | 10/1984 | Richter et al. |
| 4,484,987 A | 11/1984 | Gough |
| 4,494,950 A | 1/1985 | Fischell |
| 4,506,680 A | 3/1985 | Stokes |
| RE31,916 E | 6/1985 | Oswin et al. |
| 4,534,355 A | 8/1985 | Potter |
| 4,554,927 A | 11/1985 | Fussell |
| 4,571,292 A | 2/1986 | Liu et al. |
| 4,577,642 A | 3/1986 | Stokes |
| 4,650,547 A | 3/1987 | Gough |
| 4,663,824 A | 5/1987 | Kenmochi |

(Continued)

FOREIGN PATENT DOCUMENTS

EP     0 098 592     1/1984

(Continued)

OTHER PUBLICATIONS

Tracee Scalise Panetti "Differential effects of sphingosine 1-phosphate and lysophosphatidic acid on endothelial cells" Biochimica et Biophysica Acta 1582 (2002) 190-196.*

(Continued)

*Primary Examiner*—Christopher R Tate
*Assistant Examiner*—Aaron J Kosar
(74) *Attorney, Agent, or Firm*—Knobbe Martens Olson & Bear LLP

(57)  ABSTRACT

A biointerface membrane for an implantable device including a nonresorbable solid portion with a plurality of interconnected cavities therein adapted to support tissue ingrowth in vivo, and a bioactive agent incorporated into the biointerface membrane and adapted to modify the tissue response is provided. The bioactive agents can be chosen to induce vascularization and/or prevent barrier cell layer formation in vivo, and are advantageous when used with implantable devices wherein solutes are transported across the device-tissue interface.

25 Claims, 7 Drawing Sheets

U.S. PATENT DOCUMENTS

| | | | |
|---|---|---|---|
| 4,671,288 A | 6/1987 | Gough | |
| 4,680,268 A | 7/1987 | Clark, Jr. | |
| 4,686,044 A | 8/1987 | Behnke et al. | |
| 4,689,309 A | 8/1987 | Jones | |
| 4,702,732 A | 10/1987 | Powers et al. | |
| 4,703,756 A | 11/1987 | Gough et al. | |
| 4,711,251 A | 12/1987 | Stokes | |
| 4,721,677 A | 1/1988 | Clark | |
| 4,731,726 A | 3/1988 | Allen | |
| 4,753,652 A | 6/1988 | Langer et al. | |
| 4,757,022 A | 7/1988 | Shults et al. | |
| 4,759,828 A | 7/1988 | Young et al. | |
| 4,776,944 A | 10/1988 | Janata et al. | |
| 4,781,798 A | 11/1988 | Gough | |
| 4,803,243 A | 2/1989 | Fujimoto et al. | |
| 4,805,625 A | 2/1989 | Wyler | |
| 4,810,470 A | 3/1989 | Burkhardt et al. | |
| 4,849,458 A | 7/1989 | Reed et al. | |
| 4,852,573 A | 8/1989 | Kennedy | |
| 4,861,830 A | 8/1989 | Ward, Jr. | |
| 4,871,440 A | 10/1989 | Nagata et al. | |
| 4,883,057 A | 11/1989 | Broderick | |
| 4,889,744 A | 12/1989 | Quaid | |
| 4,890,620 A | 1/1990 | Gough | |
| 4,927,407 A | 5/1990 | Dorman | |
| 4,935,345 A | 6/1990 | Guilbeau et al. | |
| 4,953,552 A | 9/1990 | DeMarzo | |
| 4,963,595 A | 10/1990 | Ward et al. | |
| 4,970,145 A | 11/1990 | Bennetto et al. | |
| 4,974,929 A | 12/1990 | Curry | |
| 4,984,929 A | 1/1991 | Rock et al. | |
| 4,986,271 A | 1/1991 | Wilkins | |
| 4,986,671 A | 1/1991 | Sun et al. | |
| 4,994,167 A | 2/1991 | Shults et al. | |
| 5,002,572 A | 3/1991 | Picha | |
| 5,007,929 A | 4/1991 | Quaid | |
| 5,050,612 A | 9/1991 | Matsumura | |
| 5,059,654 A | 10/1991 | Hou et al. | |
| 5,067,491 A | 11/1991 | Taylor et al. | |
| 5,101,814 A | 4/1992 | Palti | |
| 5,113,871 A | 5/1992 | Viljanto et al. | |
| 5,130,231 A | 7/1992 | Kennedy et al. | |
| 5,137,028 A | 8/1992 | Nishimura | |
| 5,165,407 A | 11/1992 | Wilson et al. | |
| 5,171,689 A | 12/1992 | Kawaguri et al. | |
| 5,190,041 A | 3/1993 | Palti | |
| 5,222,980 A | 6/1993 | Gealow | |
| 5,235,003 A | 8/1993 | Ward et al. | |
| 5,249,576 A | 10/1993 | Goldberger et al. | |
| 5,264,104 A | 11/1993 | Gregg et al. | |
| 5,269,891 A | 12/1993 | Colin | |
| 5,271,736 A | 12/1993 | Picha | |
| 5,282,848 A | 2/1994 | Schmitt | |
| 5,285,513 A | 2/1994 | Kaufman et al. | |
| 5,299,571 A | 4/1994 | Mastrototaro | |
| 5,304,468 A | 4/1994 | Phillips et al. | |
| 5,310,469 A | 5/1994 | Cunningham et al. | |
| 5,314,471 A | 5/1994 | Brauker et al. | |
| 5,316,008 A | 5/1994 | Suga et al. | |
| 5,322,063 A | 6/1994 | Allen et al. | |
| 5,326,356 A | 7/1994 | Della Valle et al. | |
| 5,330,521 A | 7/1994 | Cohen | |
| 5,331,555 A | 7/1994 | Hashimoto et al. | |
| 5,340,352 A | 8/1994 | Nakanishi et al. | |
| 5,342,409 A | 8/1994 | Mullett | |
| 5,343,869 A | 9/1994 | Pross et al. | |
| 5,344,454 A | 9/1994 | Clarke et al. | |
| 5,348,788 A | 9/1994 | White | |
| 5,356,786 A | 10/1994 | Heller et al. | |
| 5,368,028 A | 11/1994 | Palti | |
| 5,372,133 A | 12/1994 | Hogen Esch | |
| 5,380,536 A | 1/1995 | Hubbell et al. | |
| 5,382,514 A * | 1/1995 | Passaniti et al. | 435/7.21 |
| 5,384,028 A | 1/1995 | Ito | |
| 5,387,327 A | 2/1995 | Khan | |
| 5,390,671 A | 2/1995 | Lord et al. | |
| 5,391,250 A | 2/1995 | Cheney et al. | |
| 5,397,848 A | 3/1995 | Yang et al. | |
| 5,411,647 A | 5/1995 | Johnson et al. | |
| 5,428,123 A | 6/1995 | Ward et al. | |
| 5,431,160 A | 7/1995 | Wilkins | |
| 5,453,278 A | 9/1995 | Chan et al. | |
| 5,458,631 A | 10/1995 | Xavier et al. | |
| 5,462,051 A | 10/1995 | Oka et al. | |
| 5,462,064 A | 10/1995 | D'Angelo et al. | |
| 5,469,846 A | 11/1995 | Khan | |
| 5,476,094 A | 12/1995 | Allen et al. | |
| 5,480,711 A | 1/1996 | Ruefer | |
| 5,484,404 A | 1/1996 | Schulman et al. | |
| 5,491,474 A | 2/1996 | Suni et al. | |
| 5,494,562 A | 2/1996 | Maley et al. | |
| 5,496,453 A | 3/1996 | Uenoyama et al. | |
| 5,497,772 A | 3/1996 | Schulman et al. | |
| 5,507,288 A | 4/1996 | Bocker et al. | |
| 5,513,636 A | 5/1996 | Palti | |
| 5,529,066 A | 6/1996 | Palti | |
| 5,531,878 A | 7/1996 | Vadgama et al. | |
| 5,540,828 A | 7/1996 | Yacynych | |
| 5,545,220 A | 8/1996 | Andrews et al. | |
| 5,545,223 A | 8/1996 | Neuenfeldt et al. | |
| 5,549,675 A | 8/1996 | Neuenfeldt et al. | |
| 5,564,439 A | 10/1996 | Picha | |
| 5,568,806 A | 10/1996 | Cheney et al. | |
| 5,569,186 A | 10/1996 | Lord et al. | |
| 5,569,462 A * | 10/1996 | Martinson et al. | 424/424 |
| 5,571,395 A | 11/1996 | Park et al. | |
| 5,575,930 A | 11/1996 | Tietje-Girault et al. | |
| 5,582,184 A | 12/1996 | Erickson et al. | |
| 5,584,876 A | 12/1996 | Bruchman et al. | |
| 5,586,553 A | 12/1996 | Halili et al. | |
| 5,589,563 A | 12/1996 | Ward et al. | |
| 5,590,651 A | 1/1997 | Shaffer et al. | |
| 5,593,440 A | 1/1997 | Brauker et al. | |
| 5,593,852 A | 1/1997 | Heller et al. | |
| 5,624,537 A | 4/1997 | Turner et al. | |
| 5,628,890 A | 5/1997 | Carter et al. | |
| 5,640,954 A | 6/1997 | Pfeiffer | |
| 5,653,756 A | 8/1997 | Clarke et al. | |
| 5,653,863 A | 8/1997 | Genshaw et al. | |
| 5,658,330 A | 8/1997 | Carlisle et al. | |
| 5,660,163 A | 8/1997 | Schulman et al. | |
| 5,683,562 A | 11/1997 | Schaffar et al. | |
| 5,686,829 A | 11/1997 | Girault | |
| 5,695,623 A | 12/1997 | Michel et al. | |
| 5,704,354 A | 1/1998 | Priedel et al. | |
| 5,706,807 A | 1/1998 | Picha | |
| 5,711,861 A | 1/1998 | Ward et al. | |
| 5,713,888 A | 2/1998 | Neuenfeldt et al. | |
| 5,733,336 A | 3/1998 | Neuenfeldt et al. | |
| 5,741,330 A * | 4/1998 | Brauker et al. | 424/423 |
| 5,743,262 A | 4/1998 | Lepper, Jr. et al. | |
| 5,749,832 A | 5/1998 | Vadgama et al. | |
| 5,756,632 A | 5/1998 | Ward et al. | |
| 5,776,324 A | 7/1998 | Usala | |
| 5,777,060 A | 7/1998 | Van Antwerp | |
| 5,779,665 A | 7/1998 | Mastrototaro et al. | |
| 5,782,912 A | 7/1998 | Brauker et al. | |
| 5,783,054 A | 7/1998 | Raguse et al. | |
| 5,787,900 A | 8/1998 | Butler et al. | |
| 5,791,344 A | 8/1998 | Schulman et al. | |
| 5,795,774 A | 8/1998 | Matsumoto et al. | |
| 5,798,065 A | 8/1998 | Picha | |
| 5,800,420 A | 9/1998 | Gross | |
| 5,800,529 A | 9/1998 | Brauker et al. | |

| | | | |
|---|---|---|---|
| 5,804,048 A | 9/1998 | Wong et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,820,622 A | 10/1998 | Gross et al. |
| 5,833,603 A | 11/1998 | Kovacs et al. |
| 5,837,728 A | 11/1998 | Purcell |
| 5,840,240 A | 11/1998 | Stenoien et al. |
| 5,851,197 A | 12/1998 | Marano et al. |
| 5,858,365 A * | 1/1999 | Faller ............ 424/184.1 |
| 5,861,019 A | 1/1999 | Sun et al. |
| 5,863,400 A | 1/1999 | Drummond et al. |
| 5,871,514 A | 2/1999 | Wiklund et al. |
| 5,882,494 A | 3/1999 | Van Antwerp |
| 5,897,578 A | 4/1999 | Wiklund et al. |
| 5,904,708 A | 5/1999 | Goedeke |
| 5,910,554 A | 6/1999 | Kempe et al. |
| 5,913,998 A | 6/1999 | Butler et al. |
| 5,914,026 A | 6/1999 | Blubaugh, Jr. et al. |
| 5,917,346 A | 6/1999 | Gord |
| 5,919,215 A | 7/1999 | Wiklund et al. |
| 5,931,814 A | 8/1999 | Alex et al. |
| 5,944,661 A | 8/1999 | Swette et al. |
| 5,957,854 A | 9/1999 | Besson et al. |
| 5,957,903 A | 9/1999 | Mirzaee et al. |
| 5,961,451 A | 10/1999 | Reber et al. |
| 5,964,261 A | 10/1999 | Neuenfeldt et al. |
| 5,964,804 A | 10/1999 | Brauker et al. |
| 5,964,993 A | 10/1999 | Blubaugh et al. |
| 5,965,380 A | 10/1999 | Heller et al. |
| 5,967,986 A | 10/1999 | Cimochowski et al. |
| 5,972,199 A | 10/1999 | Heller |
| 5,976,085 A | 11/1999 | Kimball et al. |
| 5,985,129 A | 11/1999 | Gough et al. |
| 5,999,848 A | 12/1999 | Gord et al. |
| 6,001,067 A | 12/1999 | Shults et al. |
| 6,001,471 A | 12/1999 | Bries et al. |
| 6,011,984 A | 1/2000 | Van Antwerp et al. |
| 6,013,113 A | 1/2000 | Mika |
| 6,016,448 A | 1/2000 | Busacker et al. |
| 6,049,727 A | 4/2000 | Crothall |
| 6,051,389 A | 4/2000 | Ahl et al. |
| 6,059,946 A | 5/2000 | Yukawa et al. |
| 6,063,637 A | 5/2000 | Arnold et al. |
| 6,066,083 A | 5/2000 | Slater et al. |
| 6,081,736 A | 6/2000 | Colvin et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,103,033 A | 8/2000 | Say et al. |
| 6,115,634 A | 9/2000 | Donders et al. |
| 6,119,028 A | 9/2000 | Schulman et al. |
| 6,121,009 A | 9/2000 | Heller et al. |
| 6,122,536 A | 9/2000 | Sun et al. |
| 6,134,461 A | 10/2000 | Say et al. |
| 6,135,978 A | 10/2000 | Houben et al. |
| 6,144,869 A | 11/2000 | Berner et al. |
| 6,144,871 A | 11/2000 | Saito et al. |
| 6,162,611 A | 12/2000 | Heller et al. |
| 6,167,614 B1 | 1/2001 | Tuttle et al. |
| 6,175,752 B1 | 1/2001 | Say et al. |
| 6,187,062 B1 | 2/2001 | Oweis et al. |
| 6,189,536 B1 | 2/2001 | Martinez et al. |
| 6,200,772 B1 | 3/2001 | Vadgama et al. |
| 6,201,980 B1 | 3/2001 | Darrow et al. |
| 6,206,856 B1 | 3/2001 | Mahurkar |
| 6,208,894 B1 | 3/2001 | Schulman et al. |
| 6,212,416 B1 | 4/2001 | Ward et al. |
| 6,214,185 B1 | 4/2001 | Offenbacher et al. |
| 6,230,059 B1 | 5/2001 | Duffin |
| 6,231,879 B1 | 5/2001 | Li et al. |
| 6,233,471 B1 | 5/2001 | Berner et al. |
| 6,241,863 B1 | 6/2001 | Monbouquette |
| 6,248,067 B1 | 6/2001 | Causey, III et al. |
| 6,256,522 B1 | 7/2001 | Schultz |
| 6,259,937 B1 | 7/2001 | Schulman et al. |
| 6,268,161 B1 | 7/2001 | Han et al. |
| 6,274,285 B1 | 8/2001 | Gries et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,293,925 B1 | 9/2001 | Safabash et al. |
| 6,296,615 B1 | 10/2001 | Brockway et al. |
| 6,299,578 B1 | 10/2001 | Kurnik et al. |
| 6,300,002 B1 | 10/2001 | Webb et al. |
| 6,309,351 B1 | 10/2001 | Kurnik et al. |
| 6,309,384 B1 | 10/2001 | Harrington et al. |
| 6,325,978 B1 | 12/2001 | Labuda et al. |
| 6,325,979 B1 | 12/2001 | Hahn et al. |
| 6,329,161 B1 | 12/2001 | Heller et al. |
| 6,330,464 B1 | 12/2001 | Colvin et al. |
| 6,343,225 B1 | 1/2002 | Clark, Jr. |
| 6,365,670 B1 | 4/2002 | Fry |
| 6,366,794 B1 | 4/2002 | Moussy et al. |
| 6,368,274 B1 | 4/2002 | Van Antwerp et al. |
| 6,372,244 B1 | 4/2002 | Antanavich et al. |
| 6,400,974 B1 | 6/2002 | Lesho |
| 6,405,066 B1 | 6/2002 | Essenpreis et al. |
| 6,406,066 B1 | 6/2002 | Uegane |
| 6,409,674 B1 | 6/2002 | Brockway et al. |
| 6,413,393 B1 | 7/2002 | Van Antwerp et al. |
| 6,424,847 B1 | 7/2002 | Mastrototaro et al. |
| 6,442,413 B1 | 8/2002 | Silver |
| 6,447,448 B1 | 9/2002 | Ishikawa et al. |
| 6,447,542 B1 | 9/2002 | Weadock |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,481,440 B2 | 11/2002 | Gielen et al. |
| 6,484,046 B1 | 11/2002 | Say et al. |
| 6,497,729 B1 | 12/2002 | Moussy et al. |
| 6,498,043 B1 | 12/2002 | Schulman et al. |
| 6,514,718 B2 | 2/2003 | Heller et al. |
| 6,520,997 B1 | 2/2003 | Pekkarinen et al. |
| 6,527,729 B1 | 3/2003 | Turcott |
| 6,528,584 B2 | 3/2003 | Kennedy et al. |
| 6,537,318 B1 | 3/2003 | Ita et al. |
| 6,541,107 B1 | 4/2003 | Zhong et al. |
| 6,545,085 B2 | 4/2003 | Kilgour et al. |
| 6,546,268 B1 | 4/2003 | Ishikawa et al. |
| 6,547,839 B2 | 4/2003 | Zhang et al. |
| 6,551,496 B1 | 4/2003 | Moles et al. |
| 6,558,321 B1 | 5/2003 | Burd et al. |
| 6,560,471 B1 | 5/2003 | Heller et al. |
| 6,569,521 B1 | 5/2003 | Sheridan et al. |
| 6,579,498 B1 | 6/2003 | Eglise |
| 6,585,763 B1 | 7/2003 | Keilman et al. |
| 6,587,705 B1 | 7/2003 | Kim et al. |
| 6,607,509 B2 | 8/2003 | Bobroff et al. |
| 6,613,379 B2 | 9/2003 | Ward et al. |
| 6,615,078 B1 | 9/2003 | Burson et al. |
| 6,618,934 B1 | 9/2003 | Feldman et al. |
| 6,642,015 B2 | 11/2003 | Vachon et al. |
| 6,645,181 B1 | 11/2003 | Lavi et al. |
| 6,648,821 B2 | 11/2003 | Lebel et al. |
| 6,654,625 B1 | 11/2003 | Say et al. |
| 6,683,535 B1 | 1/2004 | Utke |
| 6,694,191 B2 | 2/2004 | Starkweather et al. |
| 6,695,860 B1 | 2/2004 | Ward et al. |
| 6,699,218 B2 | 3/2004 | Flaherty et al. |

| | | |
|---|---|---|
| 6,702,857 B2 | 3/2004 | Brauker et al. |
| 6,721,587 B2 | 4/2004 | Gough |
| 6,731,976 B2 | 5/2004 | Penn et al. |
| 6,740,075 B2 | 5/2004 | Lebel et al. |
| 6,741,877 B1 | 5/2004 | Shults et al. |
| 6,773,565 B2 | 8/2004 | Kunimoto et al. |
| 6,793,632 B2 | 9/2004 | Sohrab |
| 6,793,802 B2 | 9/2004 | Lee et al. |
| 6,804,544 B2 | 10/2004 | van Antwerp et al. |
| 6,810,290 B2 | 10/2004 | Lebel et al. |
| 6,862,465 B2 | 3/2005 | Shults et al. |
| 6,895,263 B2 | 5/2005 | Shin et al. |
| 6,931,327 B2 | 8/2005 | Goode et al. |
| 6,952,604 B2 | 10/2005 | DeNuzzio et al. |
| 6,965,791 B1 | 11/2005 | Hitchcock et al. |
| 7,110,803 B2 | 9/2006 | Shults et al. |
| 7,134,999 B2 | 11/2006 | Brauker et al. |
| 7,136,689 B2 | 11/2006 | Shults et al. |
| 7,153,265 B2 | 12/2006 | Vachon |
| 7,166,074 B2 | 1/2007 | Reghabit et al. |
| 7,169,289 B2 | 1/2007 | Schulein et al. |
| 7,192,450 B2 | 3/2007 | Brauker et al. |
| 7,364,592 B2 | 4/2008 | Carr-Brendel et al. |
| 7,426,408 B2 | 9/2008 | DeNuzzio et al. |
| 2001/0044413 A1 | 11/2001 | Pierce et al. |
| 2001/0053933 A1 | 12/2001 | Phaneuf et al. |
| 2002/0019330 A1* | 2/2002 | Murray et al. ............ 514/1 |
| 2002/0022883 A1 | 2/2002 | Burg |
| 2002/0042090 A1 | 4/2002 | Heller et al. |
| 2002/0128546 A1 | 9/2002 | Silver |
| 2002/0133224 A1 | 9/2002 | Bajgar et al. |
| 2002/0151796 A1 | 10/2002 | Koulik |
| 2002/0151816 A1 | 10/2002 | Rich et al. |
| 2002/0182241 A1 | 12/2002 | Boerenstein et al. |
| 2002/0188185 A1 | 12/2002 | Sohrab |
| 2002/0193885 A1 | 12/2002 | Legeay et al. |
| 2003/0006669 A1 | 1/2003 | Pei et al. |
| 2003/0023317 A1 | 1/2003 | Brauker et al. |
| 2003/0032874 A1 | 2/2003 | Rhodes et al. |
| 2003/0036803 A1 | 2/2003 | McGhan et al. |
| 2003/0059631 A1 | 3/2003 | Al-Lamee |
| 2003/0065254 A1 | 4/2003 | Schulman et al. |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0091433 A1 | 5/2003 | Tam et al. |
| 2003/0125613 A1 | 7/2003 | Enegren et al. |
| 2003/0188427 A1 | 10/2003 | Say et al. |
| 2003/0199744 A1 | 10/2003 | Buse et al. |
| 2003/0199745 A1 | 10/2003 | Burson et al. |
| 2003/0211625 A1 | 11/2003 | Cohan |
| 2003/0217966 A1 | 11/2003 | Tapsak et al. |
| 2003/0235817 A1 | 12/2003 | Bartkowiak et al. |
| 2004/0008761 A1 | 1/2004 | Tamada et al. |
| 2004/0010207 A1 | 1/2004 | Flaherty et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0030285 A1 | 2/2004 | Lavi et al. |
| 2004/0030294 A1 | 2/2004 | Mahurkar |
| 2004/0039406 A1 | 2/2004 | Jessen |
| 2004/0045879 A1 | 3/2004 | Shults et al. |
| 2004/0068230 A1 | 4/2004 | Estes et al. |
| 2004/0106857 A1 | 6/2004 | Gough |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2004/0219664 A1 | 11/2004 | Heller et al. |
| 2005/0027180 A1 | 2/2005 | Goode et al. |
| 2005/0027181 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 | 5/2005 | DeNuzzio et al. |
| 2005/0115832 A1 | 6/2005 | Simpson et al. |
| 2005/0121322 A1 | 6/2005 | Say |
| 2005/0192557 A1 | 9/2005 | Brauker et al. |
| 2005/0211571 A1 | 9/2005 | Schulein et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0272989 A1 | 12/2005 | Shah et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036140 A1 | 2/2006 | Brister et al. |
| 2006/0198864 A1 | 9/2006 | Shults et al. |
| 2006/0200022 A1 | 9/2006 | Brauker et al. |
| 2006/0204536 A1 | 9/2006 | Shults et al. |
| 2006/0211921 A1 | 9/2006 | Brauker et al. |
| 2006/0224108 A1 | 10/2006 | Brauker et al. |
| 2006/0257995 A1 | 11/2006 | Simpson et al. |
| 2006/0257996 A1 | 11/2006 | Simpson et al. |
| 2006/0263763 A1 | 11/2006 | Simpson et al. |
| 2006/0270922 A1 | 11/2006 | Brauker et al. |
| 2006/0270923 A1 | 11/2006 | Brauker et al. |
| 2007/0027370 A1 | 2/2007 | Brauker et al. |
| 2007/0032718 A1 | 2/2007 | Shults et al. |
| 2007/0045902 A1 | 3/2007 | Brauker et al. |
| 2007/0173711 A1 | 7/2007 | Shah et al. |
| 2007/0235331 A1 | 10/2007 | Simpson et al. |
| 2008/0045824 A1 | 2/2008 | Tapsak et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2009/0036763 A1 | 2/2009 | Brauker et al. |
| 2009/0062633 A1 | 3/2009 | Brauker et al. |

FOREIGN PATENT DOCUMENTS

| | | |
|---|---|---|
| EP | 0107634 | 5/1984 |
| EP | 0 127 958 | 12/1984 |
| EP | 0 320 109 | 6/1989 |
| EP | 0 353 328 | 2/1990 |
| EP | 0 390 390 | 10/1990 |
| EP | 0 534 074 | 3/1993 |
| EP | 0535898 | 4/1993 |
| EP | 776628 A2 | 6/1997 |
| EP | 0885932 | 12/1998 |
| EP | 0817809 | 7/2002 |
| FR | 2760962 | 9/1998 |
| GB | 1442303 | 7/1976 |
| GB | 2149918 | 6/1985 |
| WO | WO 89/02720 | 4/1989 |
| WO | WO 90/00738 | 1/1990 |
| WO | WO 92/07525 | 5/1992 |
| WO | WO 92/13271 | 8/1992 |
| WO | WO 93/14693 | 8/1993 |
| WO | WO 93/19701 | 10/1993 |
| WO | WO 95/07109 | 3/1995 |
| WO | WO 96/01611 | 1/1996 |

| | | |
|---|---|---|
| WO | WO 96/14026 | 5/1996 |
| WO | WO 96/25089 | 8/1996 |
| WO | WO 96/30431 | 10/1996 |
| WO | WO 96/32076 | 10/1996 |
| WO | WO 96/36296 | 11/1996 |
| WO | WO 97/01986 | 1/1997 |
| WO | WO 97/43633 | 11/1997 |
| WO | WO 98/24358 | 6/1998 |
| WO | WO 99/56613 | 4/1999 |
| WO | WO 00/13003 | 3/2000 |
| WO | WO0019887 | 4/2000 |
| WO | WO 00/32098 | 6/2000 |
| WO | WO0033065 | 6/2000 |
| WO | WO 00/59373 | 10/2000 |
| WO | WO 00/74753 | 12/2000 |
| WO | WO 01/12158 | 2/2001 |
| WO | WO0120019 | 3/2001 |
| WO | WO0120334 | 3/2001 |
| WO | WO 01/43660 | 6/2001 |
| WO | WO 01/58348 | 8/2001 |
| WO | WO 01/88524 | 11/2001 |
| WO | WO 02/053764 | 7/2002 |
| WO | WO03101862 A1 | 12/2003 |

OTHER PUBLICATIONS

Answers.com, "xenogenic." The American Heritage Stedman's Medical Dictionary. Houghton Mifflin Company, 2002. Answers. com Nov. 7, 2006. http://www.answers.com/topic/xenogenic.*

Yanan Zhang, Ylbai Hu, and George S. Wilson "Elimination of the Acetaminophen Interference in an Implantable Glucose Sensor" Anal. Chem. 1994,66, 1183-1188.*

Ladd, M.F.C. and Palmer R.A. Structure Determination by X-ray Crystallography, 3rd ed. Plenum, 1996, Ch. 1, pp. xxi-xxiv and 1-58.*

PCT International Search Report for PCT International Application No. PCT/US2004/015909 mailed Dec. 21, 2004.

PCT International Search Report for PCT International Application No. PCT/US2004/015846, mailed on May 12, 2005.

Written Opinion of the International Searching Authority for PCT International Application No. PCT/US2004/015846, mailed on May 12, 2005.

Atanasov, et al. Biosensor for Continuous Glucose Monitoring. Biotechnology and Bioengineering 1994, 43, 262-266.

Baker, et al. Dynamic concentration challenges for biosensor characterization. Biosens Bioelectron 1993, 8, 433-441.

Bani Amer, M. M. An accurate amperometric glucose sensor based glucometer with eliminated cross-sensitivity. J Med Eng Technol 2002, 26, 208-13.

Beach, et al. Subminiature implantable potentiostat and modified commercial telemetry device for remote glucose monitoring. IEEE Transactions on Instrumentation and Measurement 1999, 48, 1239-1245.

Bindra, et al. Pulsed amperometric detection of glucose in biological fluids at a surface-modified gold electrode. Anal Chem 1989, 61, 2566-2570.

Bode, B. W. Clinical utility of the continuous glucose monitoring system. Diabetes Technol Ther 2000, 2 Suppl 1, S35-41.

Bode, et al. Continuous glucose monitoring used to adjust diabetes therapy improves glycosylated hemoglobin: a pilot study. Diabetes Res Clin Pract 1999, 46, 183-190.

Bode, et al. Using the continuous glucose monitoring system to improve the management of type 1 diabetes. Diabetes Technol Ther 2000, 2 Suppl 1. S43-8.

Bott, A. W. A Comparison of Cyclic Voltammetryand Cyclic Staircase Voltammetry. Current Separations 1997, 16:1, 23-26.

Brauker, et al. Neovascularization of synthetic membranes directed by membrane microarchitecture. J Biomed Mater Res 1995, 29, 1517-1524.

Brauker, et al. Sustained expression of high levels of human factor IX from human cells implanted within an immunoisolation device into athymic rodents. Hum Gene Ther 1998, 9, 879-888.

Brauker, J.H. Unraveling Mysteries at the Biointerface: Molecular Mediator of Inhibition of Blood Vessel Formation in the Foreign Body Capsule Revealed. Surfacts Biomaterials 2001,6, 1;5.

Bremer, et al. Benchmark data from the literature for evaluation of new glucose sensing technologies. Diabetes Technol Ther 2001, 3, 409-418.

Brunner, et al. Validation of home blood glucose meters with respect to clinical and analytical approaches. Diabetes Care 1998, 21, 585-590.

D'Arrigo, et al. Porous-Si based bioreactors for glucose monitoring and drugs production. Proc. of SPIE 2003, 4982, 178-184.

Dixon, et al. Characterization in vitro and in vivo of the oxygen dependence of an enzyme/polymer biosensor for monitoring brain glucose. J Neurosci Methods 2002, 119, 135-142.

Ernst, et al. Reliable glucose monitoring through the use of microsystem technology. Anal Bioanal Chem 2002, 373, 758-761.

Fare, et al. Functional characterization of a conducting polymer-based immunoassay system. Biosens Bioelectron 1998, 13, 459-470.

Frost, et al. Implantable chemical sensors for real-time clinical monitoring: progress and challenges. Curr Opin Chem Biol 2002, 6, 633-641.

Geller, et al. Use of an immunoisolation device for cell transplantation and tumor immunotherapy. Ann NY Acad Sci 1997, 831, 438-451.

Gerritsen, M. Problems associated with subcutaneously implanted glucose sensors. Diabetes Care 2000, 23, 143-5.

Gerritsen, et al. Influence of inflammatory cells and serum on the performance of implantable glucose sensors. J Biomed Mater Res 2001, 54, 69-75.

Gerritsen, et al. Performance of subcutaneously implanted glucose sensors for continuous monitoring. Neth J Med 1999, 54, 167-179.

Gilligan et al. Evaluation of a subcutaneous glucose sensor out to 3 months in a dog model. Diabetes Care 1994, 17:8, 882-887.

Gough, et al. Immobilized glucose oxidase in implantable glucose sensor technology. Diabetes Technol Ther 2000, 2, 377-380.

Gross, et al. Performance evaluation of the MiniMed continuous glucose monitoring system during patient home use. Diabetes Technol Ther 2000, 2, 49-56.

Gross, et al. Efficacy and reliability of the continuous glucose monitoring system. Diabetes Technol Ther 2000, 2 Suppl 1, S19-26.

Gross, Todd, "Letters to the Editor Re: Diabetes Technology & Therapeutics, 2000;2:49-56" vol. 3, No. 1, p. 130-131, 2001.

Hall, et al. Electrochemical oxidation of hydrogen peroxide at platinum electrodes. Part 1. An adsorption-controlled mechanism. Electrochimica Acta 1998, 43, 579-588.

Hall, et al. Electrochemical oxidation of hydrogen peroxide at platinum electrodes. Part II: effect of potential. Electrochimica Acta 1998, 43, 2015-2024.

Hall, et al. Electrochemical oxidation of hydrogen peroxide at platinum electrodes. Part III: Effect of temperature . Electrochimica Acta 1999, 44, 2455-2462.

Hall, et al. Electrochemical oxidation of hydrogen peroxide at platinum electrodes. Part IV: phosphate buffer dependence. Electrochimica Acta 1999, 44, 4573-4582.

Hall, et al. Electrochemical oxidation of hydrogen peroxide at platinum electrodes. Part V: inhibition by chloride. Electrochimica Acta 2000, 45, 3573-3579.

Hitchman, M. Measurement of Dissolved Oxygen. Chemical Analysis 1978, 49, 34-123.

Huang, C., O'Grady, W.E.; Yeager, E. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.

Ishikawa, et al. Initial evaluation of a 290-microm diameter subcutaneous glucose sensor: glucose monitoring with a biocompatible, flexible-wire, enzyme-based amperometric microsensor in diabetic and nondiabetic humans. J Diabetes Complications 1998, 12, 295-301.

Jensen, et al. Fast Wave Forms for Pulsed Electrochemical Detection of Glucose by Incorporation of Reduction Desorption of Oxidation Products. Analytical Chemistry 1997, 69, 1776-1781.

Johnson, et al. In vivo evaluation of an electroenzymatic glucose sensor implanted in subcutaneous tissue. Biosens Bioelectron 1992, 7, 709-714.

Jovanovic, L. The role of continuous glucose monitoring in gestational diabetes mellitus. Diabetes Technol Ther 2000, 2 Suppl 1, S67-71.

Kargol, et al. Studies on the structural properties of porous membranes: measurement of linear dimensions of solutes. Biophys Chem 2001, 91, 263-271.

Kaufman, F. R. Role of the continuous glucose monitoring system in pediatric patients. Diabetes Technol Ther 2000, 2 Suppl 1, S49-52.

Kiechle, F.L. The impact of continuous glucose monitoring on hospital point-of-care testing programs. Diabetes Technol Ther 2001, 3, 647-649.

Koschinsky, et al. Sensors for glucose monitoring: technical and clinical aspects. Diabetes Metab Res Rev 2001, 17, 113-123.

Kruger, et al. Psychological motivation and patient education: a role for continuous glucose monitoring. Diabetes Technol Ther 2000. 2 Suppl 1, S93-7.

Lee, et al. Effects of pore size, void volume, and pore connectivity on tissue responses. Society for Biomaterials 1999, 25th Annual Meeting, 171.

Lerner, et al. An implantable electrochemical glucose sensor. Ann N Y Acad Sci 1984, 428, 263-278.

Leypoldt, et al. Model of a two-substrate enzyme electrode for glucose. Anal Chem 1984, 56, 2896-2904.

Makale, et al. Tissue window chamber system for validation of implanted oxygen sensors. Am J Physiol Heart Circ Physiol 2003, 284, 1-24.

Malin, et al. Noninvasive Prediction of Glucose by Near-Infrared Diffuse Reflectance Spectroscopy. Clinical Chemistry, 45:9, 1651-1658, 1999.

Maran, et al. Continuous subcutaneous glucose monitoring in diabetic patients: a multicenter analysis. Diabetes Care 2002, 25, 347-52.

Mastrototaro, J. J.; Gross, T. M., Reproducibility of the continuous glucose monitoring system matches previous reports and the intended use of the product. *Diabetes Care*, 26:256; author reply p. 257, 2003.

Matsumoto, et al. A long-term lifetime amperometric glucose sensor with a perfluorocarbon polymer coating. Biosens Bioelectron 2001, 16, 271-276.

Miller, A. Human monocyte/macrophage activation and interleukin 1 generation by biomedical polymers. J Biomed Mater Res 1988, 23, 713-731.

Miller, et al. Generation of IL-1 like activity in response to biomedical polymer implants: a comparison of in vitro and in vivo models. J Biomed Mater Res 1989, 23, 1007-1026.

Miller, et al. In vitro stimulation of fibroblast activity by factors generated from human monocytes activated by biomedical polymers. Journal of J Biomed Mater Res 1989, 23, 911-930.

Moussy, et al. Biomaterials community examines biosensor biocompatibility. Diabetes Technol Ther 2000, 2, 473-477.

Mowery, et al. Preparation and characterization of hydrophobic polymeric films that are thromboresistant via nitric oxide release. Biomaterials 2000, 21, 9-21.

Myler, et al. Ultra-thin-polysiloxane-film-composite membranes for the optimisation of amperometric oxidase enzyme electrodes. Biosens Bioelectron 2002, 17, 35-43.

Nam, et al. A novel fabrication method of macroporous biodegradable polymer scaffolds using gas foaming salt as a porogen additive. J Biomed Mater Res 2000, 53, 1-7.

Palmisano, et al. Simultaneous monitoring of glucose and lactate by an interference and cross-talk free dual electrode amperometric biosensor based on electropolymerized thin films. Biosens Bioelectron 2000, 15, 531-539.

Pitzer, et al. Detection of hypoglycemia with the GlucoWatch biographer. Diabetes Care 2001, 24, 881-5.

Poitout, et al. A glucose monitoring system for on line estimation in man of blood glucose concentration using a miniaturized glucose sensor implanted in the subcutaneous tissue and a wearable control unit. Diabetologia 1993, 36, 658-663.

Postlethwaite, et al. Interdigitated Array Electrode as an Alternative to the Rotated Ring-Disk Electrode for Determination of the Reaction Products of Dioxygen Reduction. Analytical Chemistry 1996, 68, 2951-2958.

Ratner, B.D. Reducing capsular thickness and enhancing angiogenesis around implant drug release systems. J Control Release 2002, 78, 211-218.

Reach, Gerard, "Letters to the Editor Re: Diabetes Technology & Therapeutics, 2000;2:49-56," vol. 3, No. 1, p. 129-130, 2001.

Rhodes et al., Prediction of pocket-portable and implantable glucose enzyme electrode performance from combined species permeability and digital simulation analysis. Analytical Chemistry 1994, 66, 1520-1529.

Sansen, et al. A smart sensor for the voltammetric measurement of oxygen or glucose concentrations. Sensors and Actuators 1990, 1, 298-302.

Sansen, et al. "Glucose sensor with telemetry system." Ko, W.H. (Ed). Implantable Sensors for Closed Loop Prosthetic Systems, Ch. 12, 167-175, Futura Publishing Co. (1985).

Schmidt, et al. Glucose concentration in subcutaneous extracellular space. Diabetes Care 1993, 16, 695-700.

Schoemaker, et al. The SCGM1 System: Subcutaneous Continuous Glucose Monitoring Based on Microdialysis Technique. Diabetes Technol Ther 2003, 5, 599-608.

Shults, et al. A telemetry-instrumentation system for monitoring multiple subcutaneously implanted glucose sensors. IEEE Transactions on Biomedical Engineering 1994, 41, 937-942.

Sieminski, et al. Biomaterial-microvasculature interactions. Biomaterials 2000, 21, 2233-2241.

Skyler, J. S. The economic burden of diabetes and the benefits of improved glycemic control: the potential role of a continuous glucose monitoring system. Diabetes Technol Ther 2000, 2 Suppl 1, S7-12.

Steil, et al. Determination of plasma glucose during rapid glucose excursions with a subcutaneous glucose sensor. Diabetes Technol Ther 2003, 5, 27-31.

Tanenberg, et al. Continuous glucose monitoring system: a new approach to the diagnosis of diabetic gastroparesis. Diabetes Technol Ther 2000, 2 Suppl 1, S73-80.

Tang, et al. Fibrin(ogen) mediates acute inflammatory responses to biomaterials. J Exp Med 1993, 178, 2147-2156.

Tang, et al. Inflammatory responses to biomaterials. Am J Clin Pathol 1995, 103, 466-471.

Tang, et al. Mast cells mediate acute inflammatory responses to implanted biomaterials. Proc Natl Acad Sci U S A 1998, 95, 8841-8846.

Tang, et al. Molecular determinants of acute inflammatory responses to biomaterials. J Clin Invest 1996, 97, 1329-1334.

Thome-Duret, et. al. Modification of the sensitivity of glucose sensor implanted into subcutaneous tissue. Diabetes Metab 1996, 22, 174-178.

Tibell, et al. Survival of macroencapsulated allogeneic parathyroid tissue one year after transplantation in nonimmunosuppressed humans. Cell Transplant 2001, 10, 591-9.

Tierney, et al. The GlucoWatch biographer: a frequent automatic and noninvasive glucose monitor. Ann Med 2000, 32, 632-641.

Updike et al. Enzymatic glucose sensors: improved long-term performance in vitro and in vivo. ASAIO Journal 1994, 40, 157-163.

Updike et al. "Principles of long-term fully implanted sensors with emphasis on radiotelemetric monitoring of blood glucose from inside a subcutaneous foreign body capsule (FBC)." Fraser, D.M. (Ed.). *Biosensors in the body: continuous in vivo monitoring*, Chap. 4, pp. 117-137, John Wiley & Sons Ltd., (1997).

Updike, et al. A subcutaneous glucose sensor with improved longevity, dynamic range, and stability of calibration. Diabetes Care 2000, 23, 208-214.

Updike, et al. The enzyme electrode. Nature 1967, 214, 986-988.

Wagner, et al. A. Continuous amperometric monitoring of glucose in a brittle diabetic chimpanzee with a miniature subcutaneous electrode. Proc Natl Acad Sci U S A 1998, 95, 6379-6382.

Ward et al. A new amperometric glucose microsensor: in vitro and short-term in vivo evaluation. Biosensors & Bioelectronics 2002, 17, 181-189.

Ward, et al., Rise in background current over time in a subcutaneous glucose sensor in the rabbit: relevance to calibration and accuracy. Biosensors & Bioelectronics 2000, 15, 53-61.

Wilkins, E.; Atanasov, P.; Muggenburg, B. A., "Integrated implantable device for long-term glucose monitoring," Biosens Bioelectron 1995, 10, 485-494.

Wilson, et al. Enzyme-based biosensors for in vivo measurements. Chem Rev 2000, 100:2693-2704.

Wu, et al. In situ electrochemical oxygen generation with an immunoisolation device. Ann N Y Acad Sci 1999, 875, 105-125.

Yang, et al. Development of needle-type glucose sensor with high selectivity. Science and Actuators B 1998, 46, 249-256.

Abel, P. U.; von Woedtke, T. Biosensors for in vivo glucose measurement: can we cross the experimental stage. Biosens Bioelectron 2002, 17, 1059-1070.

Atanasov, P.; Yang, S.; Salehi, C.; Ghindilis, A. L.; Wilkins, E.; Schade, D. Implantation of a refillable glucose monitoring-telemetry device. Biosens Bioelectron 1997, 12, 669-680.

Bowman, L.; Meindl, J. D. The packaging of implantable integrated sensors. IEEE Trans Biomed Eng 1986, 33, 248-255.

Cai, Q.; Zeng, K.; Ruan, C.; Desai, T. A.; Grimes, C. A. A wireless, remote query glucose biosensor based on a pH-sensitive polymer. Anal Chem 2004, 76, 4038-4043.

Cox, D. J.; Clarke, W. L.; Gonder-Frederick, L.; Pohl, S.; Hoover, C.; Snyder, A.; Zimbelman, L.; Carter, W. R.; Bobbitt, S.; Pennebaker, J. Accuracy of perceiving blood glucose in IDDM. Diabetes Care 1985, 8, 529-536.

El-Sa'ad, L.; Yates, D. Moisture Absorption by Epoxy Resins: the Reverse Thermal Effect. Journal of Materials Science 1990, 25, 3577-3582.

Feldman, B.; Brazg, R.; Schwartz, S.; Weinstein, R. A continuous glucose sensor based on wired enzyme technology—results from a 3-day trial in patients with type 1 diabetes. Diabetes Technol Ther 2003, 5, 769-779.

Garg, S.; Schwartz, S.; Edelman, S. Improved Glucose Excursions Using an Implantable Real-Time Continuous Glucose Sensor in Adults wtih Type I Diabetes. Diabetes Care 2004, 27, 734-738.

Gilligan, B. C.; Shults, M.; Rhodes, R. K.; Jacobs, P. G.; Brauker, J. H.; Pintar, T. J.; Updike, S. J. Feasibility of continuous long-term glucose monitoring from a subcutaneous glucose sensor in humans. Diabetes Technol Ther 2004, 6, 378-386.

Heller, A. Implanted electrochemical glucose sensors for the management of diabetes. Annu Rev Biomed Eng 1999, 1, 153-175.

Heller, A. Plugging metal connectors into enzymes. Nat Biotechnol 2003, 21, 631-2.

Hrapovic, S.; Luong, J. H. Picoamperometric detection of glucose at ultrasmall platinum-based biosensors: preparation and characterization. Anal Chem 2003, 75, 3308-3315.

Hunter, I.; Jones, L., Kanigan, T., Brenan, C., Sanbol, L. Sosnowski, L. Minimally Invasive Glucose Sensor and Insulin Delivery System. MIT Home Automation and Healthcare Consortium 2000.

Jeutter, D. C. A transcutaneous implanted battery recharging and biotelemeter power switching system. IEEE Trans Biomed Eng 1982, 29, 314-321.

Kang, S. K.; Jeong, R. A.; Park, S.; Chung, T. D.; Park, S.; Kim, H. C. In vitro and short-term in vivo characteristics of a Kel-F thin film modified glucose sensor. Anal Sci 2003, 19, 1481-1486.

Kraver, K.; Guthaus, M. R.; Strong, T.; Bird, P.; Cha, G.; Hoeld, W.; Brown, R. A mixed-signal sensor interface microinstrument. Sensors and Actuators A: Physical 2001, 91, 266-277.

March, W. F. Dealing with the delay. Diabetes Technol Ther 2002, 4, 49-50.

Mastrototaro, J. J. The MiniMed continuous glucose monitoring system. Diabetes Technol Ther 2000, 2 Suppl 1, S13-8.

McCartney, L. J.; Pickup, J. C.; Rolinski, O. J.; Birch, D. J. Near-infrared fluorescence lifetime assay for serum glucose based on allophycocyanin-labeled concanavalin A. Anal Biochem 2001, 292. 216-221.

McGrath, M. J.; Iwuoha, E. I.; Diamond. D.; Smyth, M. R. The use of differential measurements with a glucose biosensor for interference compensation during glucose determinations by flow injection analysis. Biosens Bioelectron 1995, 10, 937-943.

Memoli, A.; Annesini, M. C.; Mascini, M.; Papale, S.; Petralito, S. A comparison between different immobilised glucoseoxidase-based electrodes. J Pharm Biomed Anal 2002, 29, 1045-1052.

Moatti-Sirat, D.; Capron, F.; Poitout, V.; Reach, G.; Bindra, D. S.; Zhang, Y.; Wilson, G. S.; Thevenot, D. R. Towards continuous glucose monitoring: in vivo evaluation of a miniaturized glucose sensor implanted for several days in rat subcutaneous tissue. Diabetologia 1992, 35, 224-230.

Ohara, T. J.; Rajagopalan, R.; Heller, A. "Wired" enzyme electrodes for amperometric determination of glucose or lactate in the presence of interfering substances. Anal Chem 1994, 66, 2451-2457.

Okuda, J.; Miwa, I. Mutarotase effect on micro determinations of D-glucose and its anomers with -D-glucose oxidase. Anal Biochem 1971, 43, 312-315.

Patel, H.; Li, X.; Karan, H. I. Amperometric glucose sensors based on ferrocene containing polymeric electron transfer systems—a preliminary report. Biosens Bioelectron 2003, 18, 1073-6.

Pichert, J. W.; Campbell, K.; Cox, D. J.; D'Lugin, J. J.; Moffat, J. W.; Polonsky, W. H.; CN, -.. P. o. G. D. P. S. G. Issues for the coming age of continuous glucose monitoring. Diabetes Educ 2000, 26, 969-980.

Quinn, C. A.; Connor, R. E.; Heller, A. Biocompatible, glucose-permeable hydrogel for in situ coating of implantable biosensors. Biomaterials 1997, 18, 1665-1670.

Reach, G.; Abel, P.; Fischer, U. A Method for Evaluating in vivo the Functional Characteristics of Glucose Sensors. Biosensors 1986, 2, 211-220.

Schuler, R.; Wittkampf, M.; Chemnitius, G. C. Modified gas-permeable silicone rubber membranes for covalent immobilisation of enzymes and their use in biosensor development. Analyst 1999, 124, 1181-1184.

Selam, J. L. Management of diabetes with glucose sensors and implantable insulin pumps. From the dream of the 60s to the realities of the 90s. ASAIO J 1997, 43, 137-142.

Service, R. F. Can sensors make a home in the body? Science 2002, 297, 962-3.

Shichiri, M.; Kawamori, R.; Yamasaki, Y.; Hakui, N.; Abe, H. Wearable artificial endocrine pancrease with needle-type glucose sensor. Lancet 1982, 2, 1129-1131.

Shichiri, M.; Kawamori, R.; Yamasaki, Y.; Hakui, N.; Asakawa, N.; Abe, H. Needle-type Glucose Sensor for Wearable Artificial Endocrine Pancreas. Book Implantable Sensors 1985, 197-210.

Sriyudthsak, M.; Cholapranee, T.; Sawadsaringkarn, M.; Yupongchaey, N.; Jaiwang, P. Enzyme-epoxy membrane based glucose analyzing system and medical applications. Biosens Bioelectron 1996, 11, 735-742.

Sternberg, R.; Barrau, M. B.; Gangiotti, L.; Thevenot, D. R.; Bindra, D. S.; Wilson, G. S.; Velho, G.; Froguel, P.; Reach, G. Study and development of multilayer needle-type enzyme-based glucose microsensors. Biosensors 1989, 4, 27-40.

Thome-Duret, V.; Aussedat, B.; Reach, G.; Gangnerau, M. N.; Lemonnier, F.; Klein, J. C.; Zhang, Y.; Hu, Y.; Wilson, G. S. Continuous glucose monitoring in the free-moving rat. Metabolism 1998, 47, 799-803.

Tierney, M. J.; Garg, S.; Ackerman, N. R.; Fermi, S. J.; Kennedy, J.; Lopatin, M.; Potts, R. O.; Tamada, J. A. Effect of acetaminophen on the accuracy of glucose measurements obtained with the GlucoWatch biographer. Diabetes Technol Ther 2000, 2, 199-207.

Trecroci, D. A Glimpse into the Future- Continuous Monitoring of Glucose with a Microfiber. Diabetes Interview 2002, 42-43.

Velho, G.; Froguel, P.; Sternberg, R.; Thevenot, D. R.; Reach, G. In vitro and in vivo stability of electrode potentials in needle-type glucose sensors. Influence of needle material. Diabetes 1989, 38, 164-171.

Wang, J.; Liu, J.; Chen, L.; Lu, F. Highly Selective Membrane-Free, Mediator-Free Glucose Biosensor. Anal. Chem. 1994, 66, 3600-3603.

Wang, X.; Pardue, H. L. Improved ruggedness for membrane-based amperometric sensors using a pulsed amperometric method. Anal Chem 1997, 69, 4482-4489.

Ward, W. K.; Wood, M. D.; Troupe, J. E. Understanding Spontaneous Output Fluctuations of an Amperometric Glucose Sensor: Effect of Inhalation Anesthesia and Use of a Nonenzyme Containing Electrode. ASAIO Journal 2000, 540-546.

Wientjes, K. J. C. Development of a glucose sensor for diabetic patients. 2000.
Wilkins, E.; Atanasov, P. Glucose monitoring: state of the art and future possibilities. Med Eng Phys 1995, 18, 273-288.
Wood, W., et al., Hermetic Sealing with Epoxy. Mechanical Engineering Mar. 1990, 1-3.
U.S. Appl. No. 09/447,227, filed Nov. 22, 1999.
U.S. Appl. No. 11/077,883, filed Mar. 10, 2005.
U.S. Appl. No. 11/077,740, filed Mar. 10, 2005.
U.S. Appl. No. 11/078,232, filed Mar. 10, 2005.
U.S. Appl. No. 11/077,713, filed Mar. 10, 2005.
U.S. Appl. No. 11/077,643, filed Mar. 10, 2005.
U.S. Appl. No. 11/157,746, filed Jun. 21, 2005.
U.S. Appl. No. 11/157,365, filed Jun. 21, 2005.
U.S. Appl. No. 11/158,227, filed Jun. 21, 2005.
U.S. Appl. No. 11/201,445, filed Aug. 10, 2005.
Armour et al. Dec. 1990. Application of Chronic Intravascular Blood Glucose Sensor in Dogs. Diabetes 39:1519-1526.
Bellucci et al. Jan. 1986. Electrochemical behaviour of graphite-epoxy composite materials (GECM) in aqueous salt solutions, Journal of Applied Electrochemistry, 16(1):15-22.
Bindra et al. 1991. Design and in Vitro Studies of a Needle-Type Glucose Senso for Subcutaneous Monitoring. Anal. Chem 63:1692-96.
Bobbioni-Harsch et al. 1993. Lifespan of subcutaneous glucose sensors and their performances during dynamic glycaemia changes in rats, J. Biomed. Eng. 15:457-463.
Brooks et al. "Development of an on-line glucose sensor for fermentation monitoring," Biosensors, 3:45-56 (1987/88).
Cass et al. "Ferrocene-mediated enzyme electrodes for amperometric determination of glucose," Anal. Chem., 36:667-71 (1984).
Davies, et al. 1992. Polymer membranes in clinical sensor applications. I. An overview of membrane function, Biomaterials, 13(14):971-978.
Heller, "Electrical wiring of redox enzymes," *Acc. Chem. Res.*, 23:128-134 (1990).
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Kawagoe et al. 1991. Enzyme-modified organic conducting salt microelectrode, Anal. Chem. 63:2961-2965.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Loffler et al. 1995. Separation and determination of traces of ammonia in air by means of chromatomembrane cells. Fresenius J Anal Chem 352:613-614.
Maidan et al. 1992. Elimination of Electrooxidizable Interferent-Produced Currents in Amperometric Biosensors, Analytical Chemistry, 64:2889-2896.
Mastrototaro et al. "An electroenzymatic glucose sensor fabricated on a flexible substrate," Sensors and Actuators B, 5:139-44 (1991).
McKean, et al. Jul. 7, 1988. A Telemetry Instrumentation System for Chronically Implanted Glucose and Oxygen Sensors. Transactions on Biomedical Engineering 35:526-532.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.
Pickup et al. "Implantable glucose sensors: choosing the appropriate sensing strategy," Biosensors, 3:335-346 (1987/88).

Pickup et al. "In vivo molecular sensing in diabetes mellitus: an implantable glucose sensor with direct electron transfer," Diabetologia, 32:213-217 (1989).
Pineda et al. 1996. Bone regeneration with resorbable polymeric membranes. III. Effect of poly(L-lactide) membrane pore size on the bone healing process in large defects. J. Biomedical Materials Research 31:385-394.
Pishko et al. "Amperometric glucose microelectrodes prepared through immobilization of glucose oxidase in redox hydrogels," Anal. Chem., 63:2268-72 (1991).
Poitout, et al. 1991. In Vitro and in Vivo Evaluation in Dogs of a Miniaturized Glucose Sensor, ASAIO Transactions, 37:M298-M300.
Reach et al. 1992. Can continuous glucose monitoring be used for the treatment of diabetes? Analytical Chemistry 64(5):381-386.
Rebrin et al. "Automated feedback control of subcutaneous glucose concentration in diabetic dogs," Diabetologia, 32:573-76 (1989).
Sakakida et al. 1993. Ferrocene-Mediated Needle Type Glucose Sensor Covered with Newly Designed Biocompatible Membran, Sensors and Actuators B 13-14:319-322.
Sharkawy et al. 1996. Engineering the tissue which encapsulates subcutaneous implants. I. Diffusion properties, J Biomed Mater Res, 37:401-412.
Shaw et al. "In vitro testing of a simply constructed, highly stable glucose sensor suitable for implantation in diabetic patients," Biosensors & Bioelectronics, 6:401-406 (1991).
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al. 1989. Membrane Design for Extending the Long-Life of an Implantable Glucose Sensor. Diab. Nutr. Metab. 2:309-313.
Thompson et al., In Vivo Probes: Problems and Perspectives, Toronto, Canada, Clin. Biochem., 19(5):255-261 (Oct. 1986).
Turner and Pickup, "Diabetes mellitus: biosensors for research and management," *Biosensors*, 1:85-115 (1985).
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Wilson et al. 1992. Progress toward the development of an implantable sensor for glucose. Clin. Chem. 38(9):1613-1617.
IPRP for PCT/US04/015846 filed May 18, 2004.
Office Action dated Feb. 4, 2009 in U.S. Appl. No. 10/768,889.
Office Action dated Jan. 23, 2008 in U.S. Appl. No. 09/447,227.
Office Action dated Jun. 12, 2008 in U.S. Appl. No. 09/447,227.
Office Action dated Dec. 11, 2008 in U.S. Appl. No. 09/447,227.
Office Action dated May 26, 2009 in U.S. Appl. No. 09/447,227.
Office Action dated Jun. 5, 2008 in U.S. Appl. No. 10/846,150.
Office Action dated Dec. 9, 2008 in U.S. Appl. No. 10/846,150.
Office Action dated Jun. 9, 2009 in U.S. Appl. No. 10/846,150.
Office Action dated Sep. 29, 2008 in U.S. Appl. No. 12/037,830.
Office Action dated Feb. 26, 2009 in U.S. Appl. No. 12/037,830.
Office Action dated Sep. 29, 2008 in U.S. Appl. No. 12/037,812.
Office Action dated Apr. 1, 2009 in U.S. Appl. No. 12/037,812.
Office Action dated Jul. 24, 2009 in U.S. Appl. No. 12/037,812.
Office Action dated Oct. 24, 2007 in U.S. Appl. No. 11/055,779.
Office Action dated Mar. 24, 2008 in U.S. Appl. No. 10/838,912.
Office Action dated Jul. 16, 2008 in U.S. Appl. No. 10/838,912.
Office Action mailed Jun. 5, 2008 in U.S. Appl. No. 10/838,909.
Office Action mailed Mar. 16, 2009 in U.S. Appl. No. 10/838,909.
Office Action dated May 5, 2008 in U.S. Appl. No. 11/077,713.
Office Action dated Feb. 10, 2009 in U.S. Appl. No. 11/077,713.
Office Action dated Sep. 18, 2008 in U.S. Appl. No. 11/439,630.
Office Action dated Feb. 23, 2009 in U.S. Appl. No. 11/439,630.
Office Action dated Dec. 1, 2008 in U.S. Appl. No. 11/503,367.

* cited by examiner

US 7,875,293 B2

BIOINTERFACE MEMBRANES INCORPORATING BIOACTIVE AGENTS

RELATED APPLICATION

This application is a continuation-in-part of application Ser. No. 10/647,065, filed Aug. 22, 2003, which claims the benefit of priority under 35 U.S.C. §119(e) to U.S. Provisional Application No. 60/472,673, filed May 21, 2003. This application claims the benefit of priority under 35 U.S.C. §119(e) to U.S. Provisional Application 60/544,722, filed Feb. 12, 2004. All above-referenced prior applications are incorporated by reference herein in their entirety.

FIELD OF THE INVENTION

The present invention relates generally to biointerface membranes that can be utilized with implantable devices, such as devices for the detection of analyte concentrations in a biological sample, cell transplantation devices, drug delivery devices and electrical signal delivering or measuring devices. The present invention further relates to methods for determining analyte levels using implantable devices including these membranes. More particularly, the invention relates to novel biointerface membranes, to devices and implantable devices including these membranes, and to methods for monitoring glucose levels in a biological fluid sample using an implantable analyte detection device.

BACKGROUND OF THE INVENTION

One of the most heavily investigated analyte sensing devices is the implantable glucose device for detecting glucose levels in patients with diabetes. Despite the increasing number of individuals diagnosed with diabetes and recent advances in the field of implantable glucose monitoring devices, currently used devices are unable to provide data safely and reliably for long periods of time (for example, months or years). See Moatti-Sirat et al., *Diabetologia*, 35:224-30 (1992). There are two commonly used types of implantable glucose sensing devices. These types include those that are implanted intravascularly and those that are implanted in tissue.

With reference to conventional devices that can be implanted in tissue, a disadvantage of these devices is that they tend to lose their function after the first few days to weeks following implantation. While not wishing to be bound by any particular theory, it is believed that this loss of function is due to the lack of direct contact with circulating blood to deliver sample to the tip of the probe of the implanted device. Because of these limitations, it has previously been difficult to obtain continuous and accurate glucose levels. However, such information is often extremely important to diabetic patients in ascertaining whether immediate corrective action is needed in order to adequately manage their disease.

Some medical devices, including implantable analyte measuring-devices, drug delivery devices, and cell transplantation devices require transport of solutes across the device-tissue interface for proper function. These devices generally include a membrane, herein referred to as a "cell-impermeable membrane" which encases the device or a portion of the device to prevent access by host inflammatory or immune cells to sensitive regions of the device.

A disadvantage of cell-impermeable membranes is that they often stimulate a local inflammatory response, called the foreign body response (FBR) that has long been recognized as limiting the function of implanted devices that require solute transport. Previous efforts to overcome this problem have been aimed at increasing local vascularization at the device-tissue interface, but have achieved only limited success.

FIG. 1 is a schematic drawing that illustrates a classical FBR to a conventional cell-impermeable synthetic membrane 10 implanted under the skin. There are three main layers of a FBR. The innermost FBR layer 12, adjacent to the device, is composed generally of macrophages and foreign body giant cells 14 (herein referred to as the "barrier cell layer"). These cells form a monolayer of closely opposed cells over the entire surface of a microscopically smooth membrane, a macroscopically smooth (but microscopically rough) membrane, or a microporous (i.e., average pore size of less than about 1 μm) membrane. A membrane can be adhesive or non-adhesive to cells, however, its relatively smooth surface causes the downward tissue contracture 21 (discussed below) to translate directly to the cells at the device-tissue interface 26. The intermediate FBR layer 16 (herein referred to as the "fibrous zone"), lying distal to the first layer with respect to the device, is a wide zone (about 30 to 100 μm) composed primarily of fibroblasts 18, fibrous matrixes, and contractile fibrous tissue 20. The organization of the fibrous zone, and particularly the contractile fibrous tissue 20, contributes to the formation of the monolayer of closely opposed cells due to the contractile forces 21 around the surface of the foreign body (for example, membrane 10). The outermost FBR layer 22 is loose connective granular tissue containing new blood vessels 24 (herein referred to as the "vascular zone"). Over time, this FBR tissue becomes muscular in nature and contracts around the foreign body so that the foreign body remains tightly encapsulated. Accordingly, the downward forces 21 press against the tissue-device interface 26, and without any counteracting forces, aid in the formation of a barrier cell layer 14 that blocks and/or refracts the transport of analytes 23 (for example, glucose) across the tissue-device interface 26.

A consistent feature of the innermost layers 12, 16 is that they are devoid of blood vessels. This has led to widely supported speculation that poor transport of molecules across the device-tissue interface 26 is due to a lack of vascularization near the interface. See Scharp et al., World J. Surg., 8:221-229 (1984); and Colton et al., J. Biomech. Eng., 113: 152-170 (1991). Previous efforts to overcome this problem have been aimed at increasing local vascularization at the device-tissue interface, but have achieved only limited success.

Although local vascularization can aid in sustenance of local tissue over time, the presence of a barrier cell layer 14 prevents the passage of molecules that cannot diffuse through the layer. For example, when applied to an implantable glucose-measuring device, both glucose and its phosphorylated form do not readily transit the cell membrane. Consequently, little glucose reaches the implant's membrane through the barrier cell layer. The known art purports to increase the local vascularization in order to increase solute availability. See Brauker et al., U.S. Pat. No. 5,741,330. However, it has been observed by the inventors that once the monolayer of cells (barrier cell layer) is established adjacent to a membrane, increasing angiogenesis is not sufficient to increase transport of molecules such as glucose and oxygen across the device-tissue interface 26. In fact, the barrier cell layer blocks and/or refracts the analytes 23 from transport across the device-tissue interface 26.

SUMMARY OF THE INVENTION

It has been confirmed through histological examination of biointerface membranes that the one mechanism for inhibition of molecular transport across the device-tissue interface is the barrier cell layer adjacent to the membrane. There is a strong correlation between the desired device function and the lack of formation of a barrier cell layer at the device-tissue interface. For example, glucose-measuring devices that were observed histologically to have substantial barrier cell layers were functional only 41% of the time after 12 weeks in vivo. In contrast, devices that did not have significant barrier cell layers were functional 86% of the time after 12 weeks in vivo.

Consequently, there is a need for a membrane that interferes with the formation of a barrier cell layer and protects the sensitive regions of the implantable device from host inflammatory response. The biointerface membranes of the preferred embodiments interfere with the formation of a monolayer of cells adjacent to the membrane, henceforth referred to herein as a "barrier cell layer", which interferes with the transport of oxygen, glucose, or other analytes or substances, across a device-tissue interface.

The biointerface membranes, devices including these membranes, and methods of use of these membranes according to the preferred embodiments allow for long term protection of implanted cells or drugs, as well as for obtaining continuous information regarding, for example, glucose levels of a host over extended periods of time. Because of these abilities, the biointerface membranes of the preferred embodiments can be extremely useful in implantable devices for the management of transplant patients, diabetic patients, and patients requiring frequent drug treatment.

Accordingly, in a first embodiment, a biointerface membrane including a nonresorbable solid portion and a bioactive agent is provided, wherein the nonresorbable solid portion includes a plurality of interconnected cavities adapted to support a tissue ingrowth in vivo, and wherein the bioactive agent is incorporated into the biointerface membrane and is adapted to modify a tissue response.

In an aspect of the first embodiment, the interconnected cavities and the solid portion are configured to redirect a fibrous tissue contracture in vivo, thereby interfering with formation of a barrier cell layer within or around the membrane.

In an aspect of the first embodiment, the membrane includes a micro-architecture situated within at least some of the cavities of a macro-architecture, wherein the macro-architecture includes a frame including a plurality of elongated strands of a material, wherein the strands are less than about 6 μm in all but the longest dimension.

In an aspect of the first embodiment, the solid portion is selected from the group consisting of silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene, polyvinyl alcohol, polyvinylchloride, polyvinylidene fluoride, polybutylene terephthalate, polymethylmethacrylate, polyether ether ketone, polyurethanes, cellulosic polymers, polysulfones, block copolymers thereof, and mixtures thereof. In an aspect of the first embodiment, the solid portion includes silicone.

In an aspect of the first embodiment, the bioactive agent is selected from the group consisting of anti-inflammatory agents, anti-infective agents, anesthetics, inflammatory agents, growth factors, angiogenic factors, growth factors, immunosuppressive agents, antiplatelet agents, anticoagulants, ACE inhibitors, cytotoxic agents, anti-sense molecules, and mixtures thereof. In an aspect of the first embodiment, the bioactive agent is selected from the group consisting of Sphingosine-1-phosphate, monobutyrin, Cyclosporin A, Anti-thrombospondin-2, Rapamycin, and Dexamethasone.

In an aspect of the first embodiment, the bioactive agent includes an anti-barrier cell agent. In an aspect of the first embodiment, the anti-barrier cell agent is selected from the group consisting of an anti-inflammatory agent, an anti-infective agent, an anesthetic. In an aspect of the first embodiment, the anti-barrier cell agent employs a mechanism configured to speed up a host infiltration of the interconnected cavities by inhibiting at least one of foreign body giant cells and occlusive cell layers. In an aspect of the first embodiment, the anti-barrier cell agent includes Super Oxide Dismutase Mimetic. In an aspect of the first embodiment, the anti-barrier cell agent employs an anti-inflammatory mechanism or an immunosuppressive mechanism configured to modify a wound healing of a host tissue. In an aspect of the first embodiment, the anti-barrier cell agent includes cyclosporine. In an aspect of the first embodiment, the anti-barrier cell agent includes Dexamethasone. In an aspect of the first embodiment, the anti-barrier cell agent includes Rapamycin.

In an aspect of the first embodiment, the bioactive agent includes a non-heparin based synthetic coating configured to improve a performance of blood-contacting surfaces.

In an aspect of the first embodiment, the bioactive agent includes a vascularization agent. In an aspect of the first embodiment, the vascularization agent includes an angiogenic agent configured for stimulating a neovascularization. In an aspect of the first embodiment, the vascularization agent includes Sphingosine-1-Phosphate. In an aspect of the first embodiment, the vascularization agent includes Monobutyrin. In an aspect of the first embodiment, the vascularization agent includes an anti-sense molecule.

In an aspect of the first embodiment, the vascularization agent is selected from the group consisting of Basic Fibroblast Growth Factor, Acidic Fibroblast Growth Factor, Vascular Endothelial Growth Factor, Platelet Derived Endothelial Cell Growth Factor BB, Angiopoietin-1, Transforming Growth Factor Beta, Transforming Growth Factor Alpha, Hepatocyte Growth Factor, Tumor Necrosis Factor-Alpha, Angiogenin, Interleukin-8, Hypoxia Inducible Factor-I, Angiotensin-Converting Enzyme Inhibitor Quinaprilat, Angiotropin, Thrombospondin, Peptide KGHK, Low Oxygen Tension, Lactic Acid, Insulin, Growth Hormone, and mixtures thereof.

In an aspect of the first embodiment, the vascularization agent includes a pro-inflammatory agent configured for promoting an inflammation response or an immune response. In an aspect of the first embodiment, the pro-inflammatory agent includes a xenogenic carrier. In an aspect of the first embodiment, the pro-inflammatory agent includes a Lipopolysaccharide. In an aspect of the first embodiment, the pro-inflammatory agent includes a protein.

In an aspect of the first embodiment, the bioactive agent is incorporated into the biointerface membrane via a carrier matrix. In an aspect of the first embodiment, the carrier matrix is selected from the group consisting of collagen, a particulate matrix, a non-resorbable matrix, resorbable matrix, a controlled-release matrix, a gel, and mixtures thereof.

In an aspect of the first embodiment, the bioactive agent is cross-linked with a material that forms the biointerface membrane.

In an aspect of the first embodiment, the bioactive agent is sorbed into the biointerface membrane by a process selected from the group consisting of absorption, adsorption, imbibing, and combinations thereof.

In an aspect of the first embodiment, the bioactive agent is deposited in or on a surface of the biointerface membrane by a process selected from the group consisting of coating, cavity filling, solvent casting, and combinations thereof.

In an aspect of the first embodiment, the bioactive agent is configured to be released for a time period of from about one day to about one year. In an aspect of the first embodiment, the bioactive agent is configured to be released for a time period of from about one week to about four weeks.

In a second embodiment, an analyte measuring device is provided, including a biointerface membrane including a nonresorbable solid portion and a bioactive agent, wherein the nonresorbable solid portion includes a plurality of interconnected cavities adapted to support a tissue ingrowth in vivo, and wherein the bioactive agent is incorporated into the biointerface membrane and is adapted to modify a tissue response.

In a third embodiment, an implantable glucose-measuring device is provided including a biointerface membrane including a nonresorbable solid portion and a bioactive agent, wherein the nonresorbable solid portion includes a plurality of interconnected cavities adapted to support a tissue ingrowth in vivo, and wherein the bioactive agent is incorporated into the biointerface membrane and is adapted to modify a tissue response.

In a fourth embodiment, a cell transplantation device is provided including a biointerface membrane including a nonresorbable solid portion and a bioactive agent, wherein the nonresorbable solid portion includes a plurality of interconnected cavities adapted to support a tissue ingrowth in vivo, and wherein the bioactive agent is incorporated into the biointerface membrane and is adapted to modify a tissue response.

In a fifth embodiment, an implantable drug delivery device is provided including a biointerface membrane including a nonresorbable solid portion and a bioactive agent, wherein the nonresorbable solid portion includes a plurality of interconnected cavities adapted to support a tissue ingrowth in vivo, and wherein the bioactive agent is incorporated into the biointerface membrane and is adapted to modify a tissue response. In an aspect of the fifth embodiment, the drug delivery device is selected from the group consisting of a pump, a microcapsule, and a macrocapsule.

In a sixth embodiment, an electrical signal measuring device is provided including a biointerface membrane including a nonresorbable solid portion and a bioactive agent, wherein the nonresorbable solid portion includes a plurality of interconnected cavities adapted to support a tissue ingrowth in vivo, and wherein the bioactive agent is incorporated into the biointerface membrane and is adapted to modify a tissue response.

In a seventh embodiment, an electrical pulse delivering device is provided including a biointerface membrane including a nonresorbable solid portion and a bioactive agent, wherein the nonresorbable solid portion includes a plurality of interconnected cavities adapted to support a tissue ingrowth in vivo, and wherein the bioactive agent is incorporated into the biointerface membrane and is adapted to modify a tissue response.

In an eighth embodiment, a biointerface membrane for implantation in a soft tissue is provided, the membrane including: a first domain, wherein the first domain includes a plurality of interconnected cavities and a solid portion, and wherein a substantial number of the cavities are greater than or equal to about 0.6 µm in at least one dimension; a second domain that allows a passage of an analyte and that is impermeable to cells or cell processes; and a bioactive agent incorporated into the first domain or the second domain, and which is adapted to modify an in vivo tissue response.

In an aspect of the eighth embodiment, the first domain supports a tissue ingrowth and interferes with barrier-cell layer formation.

In an aspect of the eighth embodiment, the interconnected cavities and the solid portion are configured to redirect a fibrous tissue contracture in vivo, thereby interfering with barrier cell layer formation within or around the first domain.

In an aspect of the eighth embodiment, the cavities are from about 20 to about 1000 µm in at least one dimension. In an aspect of the eighth embodiment, the cavities are from about 90 to about 370 µm in at least one dimension.

In an aspect of the eighth embodiment, the cavities are from about 0.6 to about 20 µm in at least one dimension.

In an aspect of the eighth embodiment, the cavities include a nominal pore size of between about 0.6 and 20 µm.

In an aspect of the eighth embodiment, the solid portion includes frames of elongated strands of material that are less than about 6 µm in all but the longest dimension.

In a ninth embodiment, an implantable device is provided, the device including a sensing region for sensing an analyte and a biointerface membrane adjacent to the sensing region, wherein the membrane is configured to modify an in vivo tissue response by a porous architecture and by incorporation of a bioactive agent in the membrane.

In a tenth embodiment, a biointerface membrane suitable for implantation in a soft tissue is provided, the membrane including a plurality of interconnected cavities and a solid portion, wherein the plurality of interconnected cavities and the solid portion are configured to redirect a fibrous tissue contracture, thereby interfering with barrier cell layer formation within or around the first domain, and wherein the biointerface membrane further includes a bioactive agent adapted to modify a tissue response.

In an eleventh embodiment, an implantable glucose device, the device including a nonresorbable biointerface membrane adapted to modify an in vivo tissue response, the membrane including a porous membrane architecture and having a bioactive agent incorporated therein.

In a twelfth embodiment, a biointerface membrane for use with an implantable device is provided, the biointerface membrane including: a first domain distal to the implantable device, wherein the first domain includes an open-cell configuration; a second domain proximal to the implantable device, wherein the second domain is impermeable to cells or cell processes; and a bioactive agent incorporated within the membrane.

In an aspect of the twelfth embodiment, the first domain supports tissue ingrowth and interferes with barrier-cell layer formation.

In a thirteenth embodiment, a method of monitoring an analyte concentration is provided, the method including the steps of: providing a host; providing an implantable device, the implantable device including a housing including electronic circuitry, and at least one sensing region operably connected to the electronic circuitry of the housing, the sensing region including a biointerface membrane, the biointerface membrane including a first domain distal to the implantable device, wherein the first domain includes an open-cell configuration, the biointerface membrane including a second domain proximal to the implantable device, wherein the second domain is impermeable to cells or cell processes, and wherein the biointerface membrane includes a bioactive agent incorporated into the biointerface membrane; implanting the device in the host whereby the bioactive agent is delivered to the tissue of the host; and measuring an analyte concentration.

In an aspect of the thirteenth embodiment, the device is implanted in a tissue site selected from the group consisting of subcutaneous, abdominal, peritoneal, brain, and intramedullary.

DETAILED DESCRIPTION OF THE PREFERRED EMBODIMENT

Figure 1:
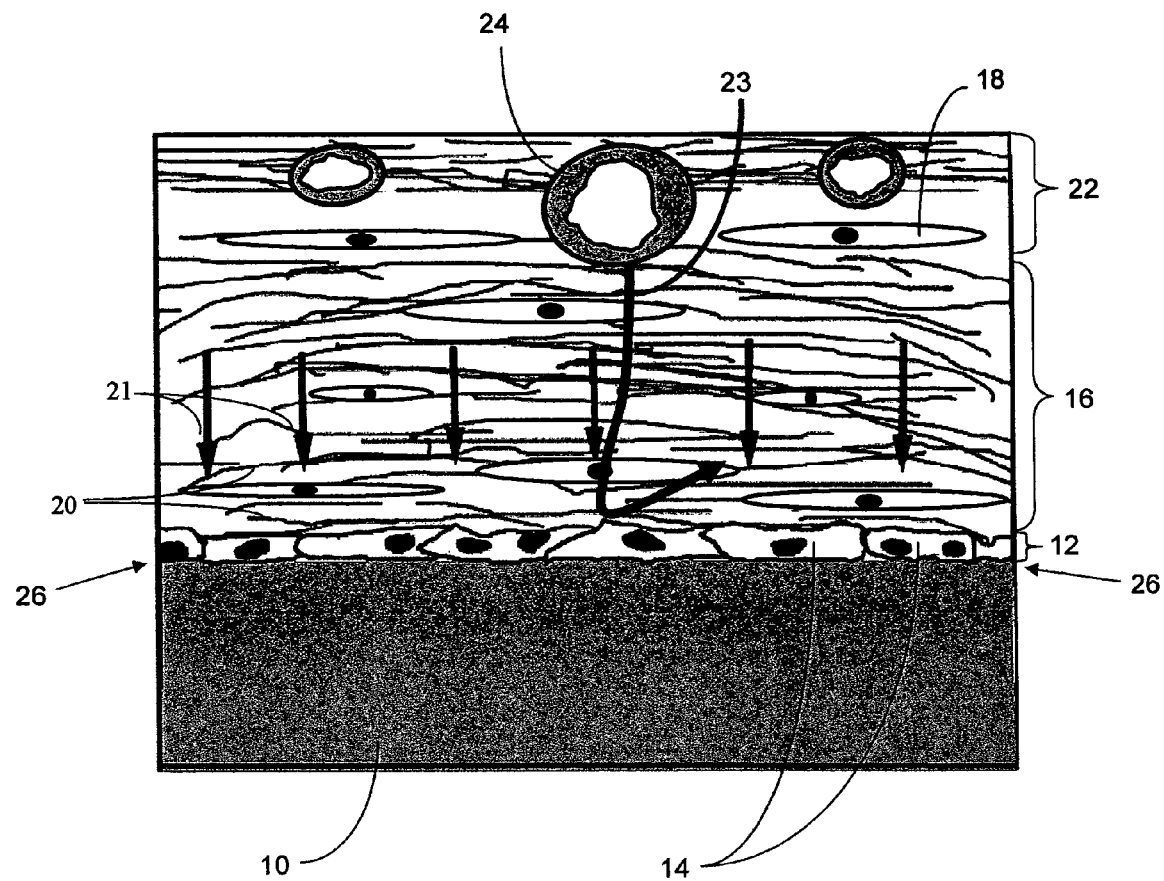
FIG. 1 is an illustration of classical three-layered foreign body response to a conventional synthetic membrane implanted under the skin.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Definitions

In order to facilitate an understanding of the preferred embodiment, a number of terms are defined below.

The term "biointerface membrane" as used herein is a broad term and is used in its ordinary sense, including, without limitation, to refer to a permeable membrane that functions as an interface between host tissue and an implantable device. In some embodiments, the biointerface membrane includes both macro-architectures and micro-architectures.

The term "barrier cell layer" as used herein is a broad term and is used in its ordinary sense, including, without limitation, to refer to a part of a foreign body response that forms a cohesive monolayer of cells (for example, macrophages and foreign body giant cells) that substantially block the transport of molecules and other substances to the implantable device.

The term "cell processes" as used herein is a broad term and is used in its ordinary sense, including, without limitation, to refer to pseudopodia of a cell.

The term "cellular attachment" as used herein is a broad term and is used in its ordinary sense, including, without limitation, to refer to adhesion of cells and/or cell processes to a material at the molecular level, and/or attachment of cells and/or cell processes to microporous material surfaces or macroporous material surfaces. One example of a material used in the prior art that encourages cellular attachment to its porous surfaces is the BIOPORE™ cell culture support marketed by Millipore (Bedford, Mass.), and as described in Brauker et al., U.S. Pat. No. 5,741,330.

The term "solid portions" as used herein is a broad term and is used in its ordinary sense, including, without limitation, to refer to portions of a membrane's material having a mechanical structure that demarcates cavities, voids, or other non-solid portions.

The term "co-continuous" as used herein is a broad term and is used in its ordinary sense, including, without limitation, to describe a solid portion or cavity wherein an unbroken curved line in three dimensions can be drawn between two sides of a membrane.

The term "biostable" as used herein is a broad term and is used in its ordinary sense, including, without limitation, to describe materials that are relatively resistant to degradation by processes that are encountered in vivo.

The terms "bioresorbable" or "bioabsorbable" as used here are broad terms and are used in their ordinary sense, including, without limitation, to describe materials that can be absorbed, or lose substance, in a biological system.

The terms "nonbioresorbable" or "nonbioabsorbable" as used here are broad terms and are used in their ordinary sense, including, without limitation, to describe materials that are not substantially absorbed, or do not substantially lose substance, in a biological system.

The terms "oxygen antenna domain" or "oxygen reservoir" as used here are broad terms and are used in their ordinary sense, including, without limitation, to refer to a domain composed of a material that has a higher oxygen solubility than an aqueous media such that it concentrates oxygen from the biological fluid surrounding a biocompatible membrane. In one embodiment, the properties of silicone (and/or silicone compositions) enable domains formed from silicone to act as an oxygen antenna domain. The oxygen antenna domain enhances function in a glucose-measuring device by applying a higher flux of oxygen to certain locations.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensor heads, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, *Myoglobin*, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni*, *Toxoplasma gondii*, *Trepenoma pallidum*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The terms "analyte-measuring device," as used herein is a broad term and is used in its ordinary sense, including, without limitation, to refer to any mechanism (for example, an enzymatic mechanism or a non-enzymatic mechanism) by which an analyte can be quantified. An example is a glucose-measuring device incorporating a membrane that contains glucose oxidase that catalyzes the conversion of oxygen and glucose to hydrogen peroxide and gluconate:

$$Glucose + O_2 \rightarrow Gluconate + H_2O_2$$

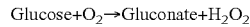

In the above reaction, for each glucose molecule consumed, there is a proportional change in the co-reactant $O_2$ and the product $H_2O_2$. Current change in either the co-reactant or the product can be monitored to determine glucose concentration.

The term "host" as used herein is a broad term and is used in its ordinary sense, including, without limitation, to refer to mammals, preferably humans.

The phrase "continuous analyte sensing" as used herein is a broad term and is used in its ordinary sense, including, without limitation, to describe the period in which monitoring of analyte concentration is continuously, continually, and/or intermittently (but regularly) performed, for example, from about every 5 seconds or less to about 10 minutes or more, preferably from about 10, 15, 20, 25, 30, 35, 40, 45, 50, 55, or 60 second to about 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50 or 9.75 minutes.

The term "sensing region" as used herein is a broad term and is used in its ordinary sense, including, without limitation, to refer to the area of an analyte-monitoring device responsible for the detection of a particular analyte. For example, the sensing region can comprise a non-conductive body, a working electrode (anode), a reference electrode, and a counter electrode (cathode) passing through and secured within the device body, forming an electrochemically reactive surface at one location on the body and an electronic connection at another location on the body, and a sensing membrane affixed to the body and covering the electrochemically reactive surface. The counter electrode preferably has a greater electrochemically reactive surface area than the working electrode. During general operation of the device, a biological sample, for example, blood or interstitial fluid, or a component thereof contacts, either directly or after passage through one or more membranes, an enzyme, for example, glucose oxidase. The reaction of the biological sample or component thereof results in the formation of reaction products that permit a determination of the analyte level, for example, glucose, in the biological sample. In some embodiments, the sensing membrane further comprises an enzyme domain, for example, an enzyme layer, and an electrolyte phase, for example, a free-flowing liquid phase comprising an electrolyte-containing fluid described further below.

The term "electrochemically reactive surface" as used herein is a broad term and is used in its ordinary sense, including, without limitation, to refer to the surface of an electrode where an electrochemical reaction takes place. In a working electrode, hydrogen peroxide produced by an enzyme-catalyzed reaction of an analyte being detected reacts can create a measurable electronic current. For example, in the detection of glucose, glucose oxidase produces $H_2O_2$ peroxide as a byproduct. the $H_2O_2$ reacts with the surface of the working electrode to produce two protons ($2H^+$), two electrons ($2e^-$) and one molecule of oxygen ($O_2$), which produces the electronic current being detected. In a counter electrode, a reducible species, for example, $O_2$ is reduced at the electrode surface so as to balance the current generated by the working electrode.

The term "sensing membrane" as used herein is a broad term and is used in its ordinary sense, including, without limitation, to refer to a permeable or semi-permeable membrane that can comprise one or more domains and that is constructed of materials having a thickness of a few microns or more, and that are permeable to reactants and/or co-reactants employed in determining the analyte of interest. As an example, a sensing membrane can comprise an immobilized glucose oxidase enzyme, which catalyzes an electrochemical reaction with glucose and oxygen to permit measurement of a concentration of glucose.

The term "proximal" as used herein, is a broad term and is used in its ordinary sense, including, without limitation, to describe a region near to a point of reference, such as an origin or a point of attachment.

The term "distal" as used herein, is a broad term and is used in its ordinary sense, including, without limitation, to describe a region spaced relatively far from a point of reference, such as an origin or a point of attachment.

The terms "operably connected" and "operably linked" as used herein are broad terms and are used in their ordinary sense, including, without limitation, to describe one or more components linked to another component(s) in a manner that facilitates transmission of signals between the components. For example, one or more electrodes can be used to detect an analyte in a sample and convert that information into a signal; the signal can then be transmitted to an electronic circuit. In this example, the electrode is "operably linked" to the electronic circuit.

The term "bioactive agent" as used herein is a broad term and is used in its ordinary sense, including, without limitation, to describe any substance that has an effect on or elicits a response from living tissue.

The term "bioerodible" or "biodegradable", as used herein, is a broad term and is used in its ordinary sense, including, without limitation, to describe materials that are enzymatically degraded or chemically degraded in vivo into simpler components.

Overview

Devices and probes that are implanted into subcutaneous tissue conventionally elicit a foreign body response (FBR), which forms a foreign body capsule (FBC), as part of the body's response to the introduction of a foreign material. Specifically, implantation of a device, for example, a glucose sensing device, can result in an acute inflammatory reaction resolving to chronic inflammation with concurrent building of fibrotic tissue, such as is described in detail above. Eventually, a mature FBC including primarily contractile fibrous tissue forms around the device. See Shanker and Greisler, Inflammation and Biomaterials in Greco RS, ed., "Implantation Biology: The Host Response and Biomedical Devices" pp 68-80, CRC Press (1994).

The FBC surrounding conventional implanted devices has been shown to hinder or block the transport of analytes across the device-tissue interface. Thus, continuous long-term analyte transport in vivo has been conventionally believed to be unreliable or impossible. For example, because the formation of a FBC isolates an implantable device in a capsule containing fluid that does not mimic the levels of analytes, such as glucose and oxygen, in the body's vasculature, long-term device function was not believed to be reliable. Additionally, the composition of a FBC can prevent stabilization of the implantable device, contributing to motion artifact that also renders results unreliable.

In contrast to conventional belief, it has been recognized that FBC formation is the dominant event surrounding long-term implantation of any device, and can be managed or manipulated to support rather than hinder or block analyte transport. It has been observed that during the early periods following implantation of an analyte-sensing device, for example a glucose-sensing device, glucose changes can be tracked in vivo, although significant time delays are typically incurred. However, after a few days to two or more weeks of implantation, these devices typically lose their function. See, for example, U.S. Pat. No. 5,791,344 and Gross et al. and "Performance Evaluation of the MiniMed Continuous Monitoring System During Patient home Use," Diabetes Technology and Therapeutics, (2000) 2(1):49-56, which have reported a glucose oxidase device, approved for use in humans by the Food and Drug Administration, that functions well for several days following implantation but loses function quickly after 3 days. These results suggest that there is sufficient vascularization and, therefore, perfusion of oxygen and glucose to support the function of an implantable glucose-measuring device for the first few days following implantation. New blood vessel formation is clearly not needed for the function of a glucose oxidase mediated electrochemical device implanted in the subcutaneous tissue for at least several days after implantation.

After several days, however, it is believed that this lack of device function is most likely due to cells, such as polymorphonuclear cells and monocytes, that migrate to the wound site during the first few days after implantation, for example, from the wounding of the tissue during implant. These cells consume local glucose and oxygen. If there is an overabundance of such cells, they can deplete glucose and/or oxygen before it is able to reach the device enzyme layer, thereby reducing the sensitivity of the device or rendering it non-functional. Further inhibition of device function can be due to inflammatory cells, for example, macrophages, that associate, for example, align at the interface, with the implantable device and physically block the transport of glucose into the device, for example, by formation of a barrier cell layer.

Additionally, these inflammatory cells can biodegrade many artificial biomaterials (some of which were, until recently, considered non-biodegradable). When activated by a foreign body, tissue macrophages degranulate, releasing hypochlorite (bleach) and other oxidative species. Hypochlorite and other oxidative species are known to break down a variety of polymers.

In order to overcome the problems associated with conventional membranes, the preferred embodiments employ biointerface membrane architectures that promote vascularization within the membrane and that interfere with barrier cell layer formation. The biointerface membranes are robust and suitable for long-term implantation and long-term analyte transport in vivo. Additionally, the membranes can be used in a variety of implantable devices, for example, analyte measuring devices, particularly glucose-measuring devices, cell transplantation devices, drug delivery devices, and electrical signal delivery and measuring devices. For example, in some embodiments of a glucose-monitoring device, the device interface can include a sensing membrane that has different domains and/or layers that can cover and protect an underlying enzyme membrane and the electrodes of the glucose-measuring device.

Biointerface Membranes

The biointerface membranes of the preferred embodiments comprise two or more domains, and incorporate a bioactive agent. A first domain is provided that includes an architecture, including cavity size, configuration, and/or overall thickness, that encourages vascular tissue ingrowth, disrupts downward tissue contracture, and/or discourages barrier cell formation. A second domain is provided that is impermeable to cells and/or cell processes. A bioactive agent is provided that is incorporated into the first and/or second domain, wherein the bioactive agent includes mechanisms that induce local vascularization and/or resist barrier cell formation.

Figure 2A:
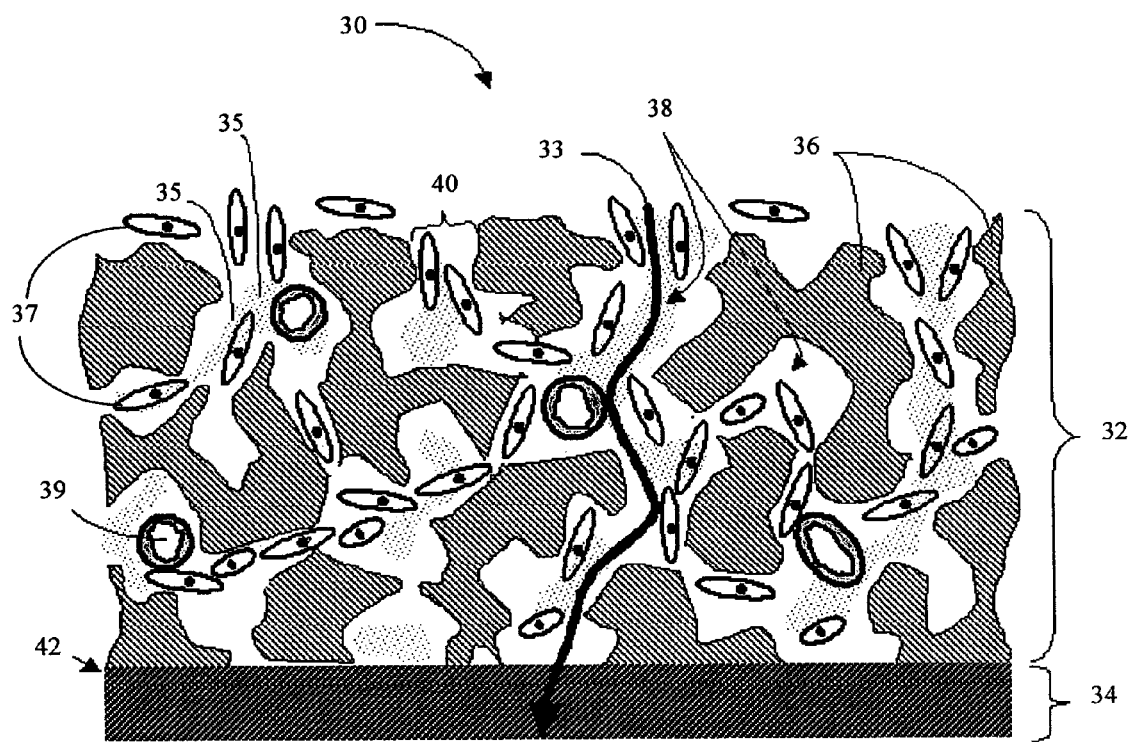
FIG. 2A is a cross-sectional schematic view of a membrane of a preferred embodiment that facilitates vascularization of the first domain without barrier cell layer formation.

FIG. 2A is a cross-sectional schematic view of a membrane 30 in vivo in one exemplary embodiment, wherein the membrane comprises a first domain 32 and second domain 34. The architecture of the membrane provides a robust, long-term implantable membrane that facilitates the transport of analytes through vascularized tissue ingrowth without the formation of a barrier cell layer.

The first domain 32 comprises a solid portion 36 and a plurality of interconnected three-dimensional cavities 38 formed therein. The cavities 38 have sufficient size and structure to allow invasive cells, such as fibroblasts 35, a fibrous matrix 37, and blood vessels 39 to enter into the apertures 40 that define the entryway into each cavity 38, and to pass through the interconnected cavities toward the interface 42 between the first and second domains. The cavities comprise an architecture that encourages the ingrowth of vascular tissue in vivo, as indicated by the blood vessels 39 formed throughout the cavities. Because of the vascularization within the cavities, solutes 33 (for example, oxygen, glucose and other analytes) pass through the first domain with relative ease, and/or the diffusion distance (namely, distance that the glucose diffuses) is reduced.

The biointerface membranes of the preferred embodiments preferably include a bioactive agent, which is incorporated into at least one of the first and second domains 32, 34 of the biointerface membrane, or which is incorporated into the device and adapted to diffuse through the first and/or second domains, in order to modify the tissue response of the host to the membrane. The architectures of the first and second domains have been shown to support vascularized tissue ingrowth, to interfere with and resist barrier cell layer formation, and to facilitate the transport of analytes across the membrane. However, the bioactive agent can further enhance vascularized tissue ingrowth, resistance to barrier cell layer formation, and thereby facilitate the passage of analytes 33 across the device-tissue interface 42.

Architecture of the First Domain

The first domain of the biointerface membrane includes an architecture that supports tissue ingrowth, disrupts contractile forces typically found in a foreign body response, encourages vascularity within the membrane, and disrupts the formation of a barrier cell layer. The first domain, also referred to as the cell disruptive domain, comprises an open-celled configuration comprising interconnected cavities and solid portions. The distribution of the solid portion and cavities of the first domain preferably includes a substantially co-continuous solid domain and includes more than one cavity in three dimensions substantially throughout the entirety of the first domain. Generally, cells can enter into the cavities; however, they cannot travel through or wholly exist within the solid portions. The cavities permit most substances to pass through, including, for example, cells and molecules.

Figure 2B:
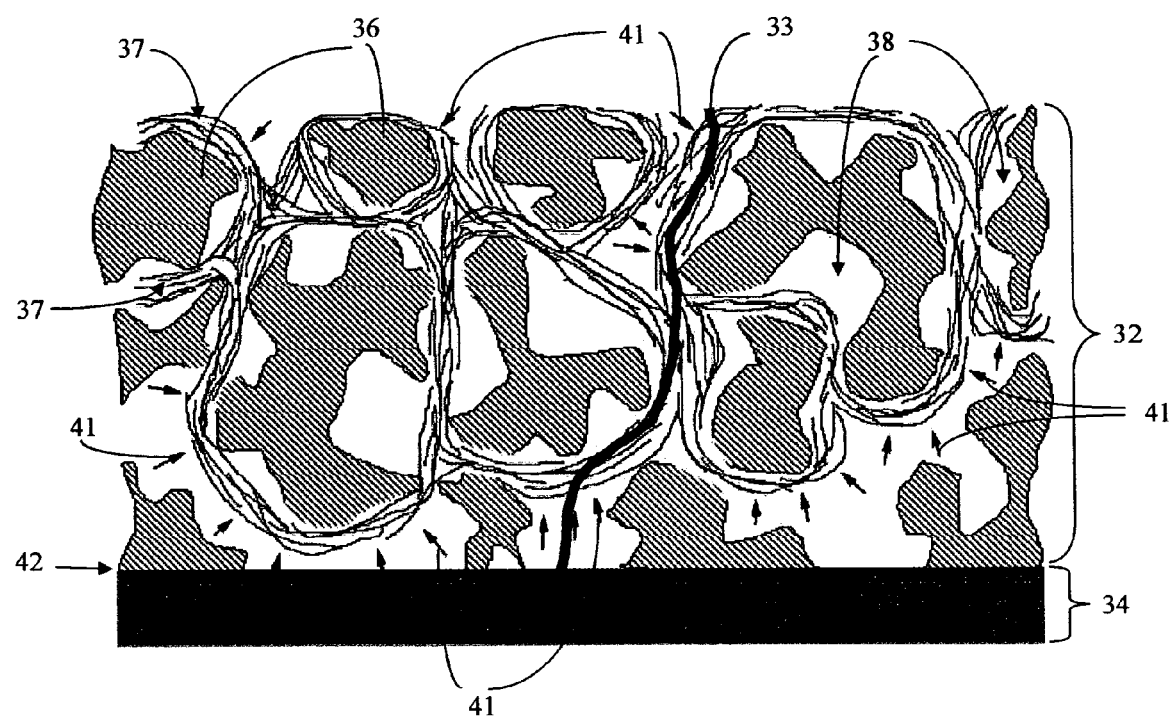
FIG. 2B is a cross-sectional schematic view of the membrane of FIG. 2A showing contractile forces caused by the fibrous tissue of the FBR.

Reference is now made to FIG. 2B, which is an illustration of the membrane of FIG. 2A, showing contractile forces caused by the fibrous tissue, for example, from the fibroblasts and fibrous matrix, of the FBR. Specifically, the architecture of the first domain, including the cavity interconnectivity and multiple-cavity depth, (namely, two or more cavities in three dimensions throughout a substantial portion of the first domain) can affect the tissue contracture that typically occurs around a foreign body.

A contraction of the FBC around the device as a whole produces downward forces on the device can be helpful in reducing motion artifacts, such as are described in copending U.S. patent application Ser. No. 10/646,333, filed Aug. 22, 2003 and entitled "OPTIMIZED DEVICE GEOMETRY FOR AN IMPLANTABLE GLUCOSE DEVICE," which is incorporated herein in its entirety by reference. The architecture of the first domain of the biointerface membrane, including the interconnected cavities and solid portion, is advantageous because the contractile forces caused by the downward tissue contracture that can otherwise cause cells to flatten against the device and occlude the transport of analytes, is instead translated to, disrupted by, and/or counteracted by the forces 41 that contract around the solid portions 36 (for example, throughout the interconnected cavities 38) away from the device. That is, the architecture of the solid portions 36 and cavities 38 of the first domain cause contractile forces 41 to disperse away from the interface between the first domain 32 and second domain 34. Without the organized contracture of fibrous tissue toward the tissue-device interface 42 typically found in a FBC (FIG. 1), macrophages and foreign body giant cells do not form a substantial monolayer of cohesive cells (namely, a barrier cell layer) and therefore the transport of molecules across the second domain and/or membrane is not blocked, as indicated by free transport of analyte 33 through the first and second domains in FIGS. 2A and 2B.

Various methods are suitable for use in manufacturing the first domain in order to create an architecture with preferred dimensions and overall structure. The first domain can be manufactured by forming particles, for example, sugar granules, salt granules, and other natural or synthetic uniform or non-uniform particles, in a mold, wherein the particles have shapes and sizes substantially corresponding to the desired cavity dimensions. In some methods, the particles are made to coalesce to provide the desired interconnectivity between the cavities. The desired material for the solid portion can be introduced into the mold using methods common in the art of polymer processing, for example, injecting, pressing, vacuuming, or pouring. After the solid portion material is cured or solidified, the coalesced particles are then dissolved, melted, etched, or otherwise removed, leaving interconnecting cavities within the solid portion. In such embodiments, sieving can be used to determine the dimensions of the particles, which substantially correspond to the dimensions of resulting cavities. In sieving, also referred to as screening, the particles are added to the sieve and then shaken to produce overs and unders. The overs are the particles that remain on the screen and the unders are the particles that pass through the screen. Other methods and apparatus known in the art are also suitable for use in determining particle size, for example, air classifiers, which apply opposing air flows and centrifugal forces to separate particles having sizes down to 2 µm, can be used to determine particle size when particles are smaller than 100 µm.

In one embodiment, the cavity size of the cavities 38 of the first domain is substantially defined by the particle size(s) used in creating the cavities. In some embodiments, the particles used to form the cavities can be substantially spherical, thus the dimensions below describe a diameter of the particle and/or a diameter of the cavity. In some alternative embodiments, the particles used to form the cavities can be non-spherical (for example, rectangular, square, diamond, or other geometric or non-geometric shapes), thus the dimensions below describe one dimension (for example, shortest, average, or longest) of the particle and/or cavity.

In some embodiments, a variety of different particle sizes can be used in the manufacture of the first domain. In some embodiments, the dimensions of the particles can be somewhat smaller or larger than the dimensions of the resulting cavities, due to dissolution or other precipitation that can occur during the manufacturing process.

Although one method of manufacturing porous domains is described above, a variety of methods known to one of ordinary skill in the art can be employed to create the structures of preferred embodiments. For example, molds can be used in the place of the particles described above, such as coral, self-assembly beads, etched or broken silicon pieces, glass frit pieces, and the like. The dimensions of the mold can define the cavity sizes, which can be determined by measuring the cavities of a model final product, and/or by other measuring techniques known in the art, for example, by a bubble point test. In U.S. Pat. No. 3,929,971, Roy discloses a method of making a synthetic membrane having a porous microstructure by converting calcium carbonate coral materials to hydroxyapatite while at the same time retaining the unique microstructure of the coral material.

Other methods of forming a three-dimensional first domain can be used, for example holographic lithography, stereolithography, and the like, wherein cavity sizes are defined and precisely formed by the lithographic or other such process to form a lattice of unit cells, as described in co-pending U.S. Provisional Patent Application 60/544,722, entitled "Macro-Micro Architecture for Biointerface Membrane," which is incorporated herein by reference in its entirety and as described by Pekkarinen et al. in U.S. Pat. No. 6,520,997, which discloses a photolithographic process for creating a porous membrane.

The first domain 32 can be defined using alternative methods. In an alternative preferred embodiment, fibrous nonwoven or woven materials, or other such materials, such as electrospun, scattered, or aggregate materials, are manufactured by forming the solid portions without particularly defining the cavities therebetween. Accordingly, in these alternative embodiments, structural elements that provide the three-dimensional conformation can include fibers, strands, globules, cones, and/or rods of amorphous or uniform geometry that are smooth or rough. These elements are hereinafter referred to as "strands." The solid portion of the first domain can include a plurality of strands, which generally define apertures formed by a frame of the interconnected strands. The apertures of the material form a framework of interconnected cavities. Formed in this manner, the first domain is defined by a cavity size of about 0.6 to about 1000 µm in at least one dimension.

Referring to the dimensions and architecture of the first domain 32, the porous biointerface materials can be loosely categorized into at least two groups: those having a micro-architecture and those having a macro-architecture.

FIGS. 2A and 2B illustrate one preferred embodiment wherein the biointerface material includes a macro-architecture as defined herein. In general, the cavity size of a macro-architecture provides a configuration and overall thickness that encourages vascular tissue ingrowth and disrupts tissue contracture that is believed to cause barrier cell formation in vivo (as indicated by the blood vessels 39 formed throughout the cavities), while providing a long-term, robust structure. Referring to the macro-architecture, a substantial number of the cavities 38, defined using any of the methods described above, are greater than or equal to about 20 µm in one dimension. In some other embodiments, a substantial number of the cavities are greater than or equal to about 30, 40, 50, 60, 70, 80, 90, 100, 120, 140, 160, 180, 200, 240, 280, 320, 360, 400, 500, 600, 700 µm, and preferably less than about 1000 µm in one dimension. Although the macro-architecture is associated the numerous advantages as described above, in some embodiments it can create an opportunity for foreign body giant cells to flatten against the second domain and/or implantable device 34 and potentially create a layer of barrier cells that can block some or all analyte transport. It is therefore advantageous to incorporate a bioactive agent into the macro-architecture in order to modify the tissue response of the host to the membrane.

The biointerface material can also be formed with a micro-architecture as defined herein. Generally, at least some of the cavities of a micro-architecture have a sufficient size and structure to allow inflammatory cells to partially or completely enter into the cavities. However, in contrast to the macro-architecture, the micro-architecture does not allow extensive ingrowth of vascular and connective tissues within the cavities. Therefore, in some embodiments, the micro-architecture of preferred embodiments is defined by the actual size of the cavity, wherein the cavities are formed from a mold, for example, such as described in more detail above. However, in the context of the micro-architecture it is preferable that the majority of the mold dimensions, whether particles, beads, crystals, coral, self-assembly beads, etched or broken silicon pieces, glass frit pieces, or other mold elements that form cavities, are less than about 20 µm in at least one dimension.

In some alternative micro-architecture embodiments, wherein the biointerface material is formed from a substantially fibrous material, the micro-architecture is defined by a strand size of less than 6 µm in all but the longest dimension, and a sufficient number of cavities are provided of a size and structure to allow inflammatory cells, for example, macrophages, to completely enter through the apertures that define the cavities, without extensive ingrowth of vascular and connective tissues.

In certain embodiments, the micro-architecture is characterized, or defined, by standard pore size tests, such as the bubble point test. The micro-architecture is selected with a nominal pore size of from about 0.6 µm to about 20 µm. In some embodiments, the nominal pore size from about 1, 2, 3, 4, 5, 6, 7, 8, or 9 µm to about 10, 11, 12, 13, 14, 15, 16, 17, 18, or 19 µm. It has been found that a porous polymer membrane having an average nominal pore size of about 0.6 to about 20 µm functions satisfactorily in creating a vascular bed within the micro-architecture at the device-tissue interface. The term "nominal pore size" in the context of the micro-architecture 52 in certain embodiments is derived from methods of analysis common to membrane, such as the ability of the membrane to filter particles of a particular size, or the resistance of the membrane to the flow of fluids. Because of the amorphous, random, and irregular nature of most of these commercially available membranes, the "nominal pore size" designation may not actually indicate the size or shape of the apertures and cavities, which in reality have a high degree of variability. Accordingly, as used herein with reference to the micro-architecture, the term "nominal pore size" is a manufacturer's convention used to identify a particular membrane of a particular commercial source which has a certain bubble point; as used herein, the term "pore" does not describe the size of the cavities of the material in the preferred embodiments. The bubble point measurement is described in Pharmaceutical Technology, May 1983, pp. 36 to 42.

While not wishing to be bound by any particular theory, it is believed that biointerface membranes with a micro-architecture as defined herein, are advantageous for inducing close vascular structures, maintaining rounded inflammatory cell morphology, preventing barrier cell layer formation, and preventing organized fibroblasts and connective tissue from entering into the membrane. In some instances, crushing and delamination of a micro-architecture biointerface material can occur, which allows foreign body giant cells to flatten against the implantable device and potentially create a barrier layer of cells that block some or all analyte transport. It can therefore be advantageous to incorporate a bioactive agent into the micro-architecture in order to modify the tissue response of the host to the membrane.

The optimum dimensions, architecture (for example, micro-architecture or macro-architecture), and overall structural integrity of the membrane can be adjusted according to the parameters of the device that it supports. For example, if the membrane is employed with a glucose-measuring device, the mechanical requirements of the membrane can be greater for devices having greater overall weight and surface area when compared to those that are relatively smaller.

With regard to the depth of cavities, improved vascular tissue ingrowth is observed when the first domain has a thickness that accommodates a depth of at least two cavities throughout a substantial portion of the thickness. Improved vascularization results at least in part from multi-layered interconnectivity of the cavities, such as in the preferred embodiments, as compared to a surface topography such as seen in the prior art, for example, wherein the first domain has a depth of only one cavity throughout a substantial portion thereof. The multi-layered interconnectivity of the cavities enables vascularized tissue to grow into various layers of cavities in a manner that provides mechanical anchoring of the device with the surrounding tissue. Such anchoring resists movement that can occur in vivo, which results in reduced sheer stress and scar tissue formation. The optimum depth or number of cavities can vary depending upon the parameters of the device that it supports. For example, if the membrane is employed with a glucose-measuring device, the anchoring that is required of the membrane is greater for devices having greater overall weight and surface area as compared to those that are relatively smaller.

The thickness of the first domain can be optimized for decreased time-to-vascularize in vivo, that is, vascular tissue ingrowth can occur somewhat faster with a membrane that has a thin first domain as compared to a membrane that has a relatively thicker first domain. Decreased time-to-vascularize results in faster stabilization and functionality of the biointerface in vivo. For example, in a subcutaneous implantable glucose device, consistent and increasing functionality of the device is at least in part a function of consistent and stable glucose transport across the biointerface membrane, which is at least in part a function of the vascularization thereof. Thus, quicker start-up time and/or shortened time lag (as when, for example, the diffusion path of the glucose through the membrane is reduced) can be achieved by decreasing the thickness of the first domain.

The thickness of the first domain is typically form about 20 µm to about 2000 µm, preferably from about 30, 40, 50, 60, 70, 80, 90, or 100 µm to about 800, 900, 1000, 1100, 1200, 1300, 1400, 1500, 1600, 1700, 1800, or 1900 µm, and most preferably from about 150, 200, 250, 300, 350, or 400 µm to about 450, 500, 550, 600, 650, 700, or 750 µm. However, in some alternative embodiments a thinner or thicker cell disruptive domain (first domain) can be desired.

The solid portion preferably includes one or more materials such as silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, di-block, tri-block, alternating, random and graft copolymers. In some embodiments, the material selected for the first domain is an elastomeric material, for example, silicone, which is able to absorb stresses that can occur in vivo, such that sheer and other environmental forces are significantly minimized at the second domain. The solid portion can comprises a silicone composition with a hydrophile such as Polyethylene Glycol (PEG) covalently incorporated or grafted therein, such as described in co-pending U.S. patent application Ser. No. 10/695,636, filed Oct. 28, 2003, and entitled, "SILICONE COMPOSITION FOR BIOCOMPATIBLE MEMBRANE," which is incorporated herein by reference in its entirety. Additionally, elastomeric materials with a memory of the original configuration can withstand greater stresses without affecting the configuration, and thus the function, of the device.

The first domain can include a macro-architecture and a micro-architecture located within at least a portion of the macro-architecture, such as is described in co-pending U.S. Provisional Patent Application 60/544,722, entitled, "BIOINTERFACE WITH MACRO- AND MICRO-ARCHITECTURE," which is incorporated herein by reference in its entirety. For example, the macro-architecture includes a porous structure with interconnected cavities such as described with reference to the solid portion of the first domain, wherein at least some portion of the cavities of the first domain are filled with the micro-architecture that includes a fibrous or other fine structured material that aids in preventing formation of a barrier cell layer, for example in pockets in the bottom of the cavities of the macro-architecture adjacent to the implantable device.

In certain embodiments, other non-resorbable implant materials can be used in forming the first domain, including but not limited to, metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(l-lysine), poly (L-lactic acid), hydroxyethylmetharcrylate, hydroxyapeptite, alumina, zirconia, carbon fiber, aluminum, calcium phosphate, titanium, titanium alloy, nintinol, stainless steel, and CoCr alloy.

Architecture of the Second Domain

FIGS. 2A and 2B, illustrate the second domain of the membrane. The second domain is impermeable to cells or cell processes, and is composed of a biostable material. In one embodiment, the second domain is comprised of polyurethane and a hydrophilic polymer, such as is described in co-pending U.S. application Ser. No. 09/916,858 filed Jul. 27, 2001, which is incorporated herein by reference in its entirety. Alternatively, the hydrophilic polymer can include polyvinylpyrrolidone. Alternatively, the second domain is polyurethane comprising about 5 weight percent or more polyvinylpyrrolidone and about 45 weight percent or more polyvinylpyrrolidone. Alternatively, the second domain comprises about 20 weight percent or more polyvinylpyrrolidone and about 35 weight percent or more polyvinylpyrrolidone. Alternatively, the second domain is polyurethane comprising about 27 weight percent polyvinylpyrrolidone. In certain embodiments, however, the second domain can comprise about 5 weight percent or more than about 45 weight percent polyvinylpyrrolidone.

Alternatively, the second domain can be formed from materials such as copolymers or blends of copolymers with hydrophilic polymers such as polyvinylpyrrolidone (PVP), polyhydroxyethyl methacrylate, polyvinylalcohol, polyacrylic acid, polyethers such as polyethylene glycol, and block copolymers thereof, including, for example, di-block, tri-block, alternating, random and graft copolymers (block copolymers are disclosed in U.S. Pat. Nos. 4,803,243 and 4,686,044). In some embodiments, the second domain can comprise a silicone composition with a hydrophile such as Polyethylene Glycol (PEG) covalently incorporated or grafted therein, such as described in co-pending U.S. patent application Ser. No. 10/695,636, entitled, "SILICONE COMPOSITION FOR BIOCOMPATIBLE MEMBRANE," which is incorporated herein by reference in its entirety. In one embodiment, the second domain is comprised of a silicone copolymer including a hydrophilic component, which can be formed as a unitary structure with the first domain or a separate structure adhered thereto.

In general, the materials preferred for the second domain prevent or hinder cell entry or contact with device elements underlying the membrane and prevent or hinder the adherence of cells, thereby further discouraging formation of a barrier cell layer. Additionally, because of the resistance of the materials to barrier cell layer formation, membranes prepared therefrom are robust long-term in vivo.

The thickness of the cell impermeable biomaterial of the second domain (also referred to as a cell impermeable domain) is typically about 1 μm or more, preferably from about 1, 5, 10, 15, 20, 25, 30, 35, 40, 45, or 50 μm to about 55, 60, 65, 70, 75, 80, 85, 90, 95, 100, 110, 120, 130, 140, 150, 160, 170, 180, 190, or 200 μm. In some embodiments, thicker or thinner cell impermeable domains can be desired. Alternatively, the function of the cell impermeable domain is accomplished by the implantable device, or a portion of the implantable device, which may or may not include a distinct domain or layer.

The characteristics of the cell impermeable membrane prevent or hinder cells from entering the membrane, but permit or facilitate transport of the analyte of interest or a substance indicative of the concentration or presence of the analyte. Additionally the second domain, similar to the first domain, is preferably constructed of a biodurable material (for example, a material durable for a period of several years in vivo) that is impermeable to host cells, for example, macrophages, such as described above.

In embodiments wherein the biointerface membrane is employed in an implantable glucose-measuring device, the biointerface membrane is permeable to oxygen and glucose or a substance indicative of the concentration of glucose. In embodiments wherein the membrane is employed in a drug delivery device or other device for delivering a substance to the body, the cell impermeable membrane is permeable to the drug or other substance dispensed from the device. In embodiments wherein the membrane is employed for cell transplantation, the membrane is semi-permeable, for example, impermeable to immune cells and soluble factors responsible for rejecting transplanted tissue, but permeable to the ingress of glucose and oxygen for the purpose of sustaining the transplanted tissue; additionally, the second domain is permeable to the egress of the gene product of interest (for example, insulin).

The cell disruptive (first) domain and the cell impermeable (second) domain can be secured to each other by any suitable method as is known in the art. For example, the cell impermeable domain can simply be layered or cast upon the porous cell disruptive domain so as to form a mechanical attachment. Alternatively, chemical and/or mechanical attachment methods can be suitable for use. Chemical attachment methods can include adhesives, glues, lamination, and/or wherein a thermal bond is formed through the application of heat and pressure, and the like. Suitable adhesives are those capable of forming a bond between the materials that make up both the barrier cell disruptive domain and the cell impermeable domain, and include liquid and/or film applied adhesives. An appropriate material can be designed that can be used for preparing both domains such that the composite is prepared in one step, thereby forming a unitary structure. For example, when the cell disruptive domain and the cell impermeable domain comprise silicone, the materials can be designed so that they can be covalently cured to one another. However in some embodiments wherein the second domain comprises a part of the implantable device, it can be attached to or simply lie adjacent to the first domain.

In some embodiments wherein an adhesive is employed, the adhesive can comprise a biocompatible material. However, in some embodiments adhesives not generally considered to have a high degree of biocompatibility can also be employed. Adhesives with varying degrees of biocompatibility suitable for use include acrylates, for example, cyanoacrylates, epoxies, methacrylates, polyurethanes, and other polymers, resins, and crosslinking agents as are known in the art. In some embodiments, a layer of non-woven material (such as ePTFE) is cured to the first domain after which the material is bonded to the second domain, which allows a good adhesive interface between the first and second domains using a biomaterial known to respond well at the tissue-device interface, for example.

Bioactive Agents

The biointerface membranes of the preferred embodiments preferably include a bioactive agent, which is incorporated into at least one of the first and second domains of the biointerface membrane, or which is incorporated into the device and adapted to diffuse through the first and/or second domains, in order to modify the tissue response of the host to the membrane. The architectures of the first and second domains support vascularized tissue growth in or around the biointerface membrane, interfere with and resist barrier cell layer formation, and allow the transport of analytes across the membrane. However, certain outside influences, for example, faulty surgical techniques, acute or chronic movement of the implant, or other surgery-, patient-, and/or implantation site-related conditions, can create acute and/or chronic inflammation at the implant site. When this occurs, the biointerface membrane architecture alone may not be sufficient to overcome the acute and/or chronic inflammation. Alternatively, the membrane architecture can benefit from additional mechanisms that aid in reducing this acute and/or chronic inflammation that can produce a barrier cell layer and/or a fibrotic capsule surrounding the implant, resulting in compromised solute transport through the membrane.

In general, the inflammatory response to biomaterial implants can be divided into two phases. The first phase consists of mobilization of mast cells and then infiltration of predominantly polymorphonuclear (PMN) cells. This phase is termed the acute inflammatory phase. Over the course of days to weeks, chronic cell types that comprise the second phase of inflammation replace the PMNs. Macrophage and lymphocyte cells predominate during this phase. While not wishing to be bound by any particular theory, it is believed that short-term stimulation of vascularization, or short-term inhibition of scar formation or barrier cell layer formation, provides protection from scar tissue formation, thereby providing a stable platform for sustained maintenance of the altered foreign body response.

Accordingly, bioactive intervention can modify the foreign body response in the early weeks of foreign body capsule formation, thereby fundamentally altering the long-term behavior of the foreign body capsule. Additionally, it is believed that the biointerface membranes of the preferred embodiments can advantageously benefit from bioactive intervention to overcome sensitivity of the membrane to implant procedure, motion of the implant, or other factors, which are known to otherwise cause inflammation, scar formation, and hinder device function in vivo.

In general, bioactive agents that are believed to modify tissue response include anti-inflammatory agents, anti-infective agents, anesthetics, inflammatory agents, growth factors, angiogenic (growth) factors, adjuvants, wound factors, resorbable device components, immunosuppressive agents, antiplatelet agents, anticoagulants, ACE inhibitors, cytotoxic agents, anti-barrier cell compounds, vascularization compounds, anti-sense molecules, and the like. In some embodiments, preferred bioactive agents include S1P (Sphingosine-1-phosphate), Monobutyrin, Cyclosporin A, Anti-thrombospondin-2, Rapamycin (and its derivatives), and Dexamethasone. However, other bioactive agents, biological materials (for example, proteins), or even non-bioactive substances can be preferred for incorporation into the membranes of preferred embodiments.

Bioactive agents suitable for use in the preferred embodiments are loosely organized into two groups: anti-barrier cell agents and vascularization agents. These designations reflect functions that are believed to provide short-term solute transport through the biointerface membrane, and additionally extend the life of a healthy vascular bed and hence solute transport through the biointerface membrane long term in vivo. However, not all bioactive agents can be clearly categorized into one or other of the above groups; rather, bioactive agents generally comprise one or more varying mechanisms for modifying tissue response and can be generally categorized into one or both of the above-cited categories.

Anti-Barrier Cell Agents

Generally, anti-barrier cell agents include compounds exhibiting affects on macrophages and foreign body giant cells (FBGCs). It is believed that anti-barrier cell agents prevent closure of the barrier to solute transport presented by macrophages and FBGCs at the device-tissue interface during FBC maturation.

Anti-barrier cell agents generally include mechanisms that inhibit foreign body giant cells and/or occlusive cell layers. For example, Super Oxide Dismutase (SOD) Mimetic, which utilizes a manganese catalytic center within a porphyrin like molecule to mimic native SOD and effectively remove superoxide for long periods, thereby inhibiting FBGC formation at the surfaces of biomaterials in vivo, is incorporated into a biointerface membrane of a preferred embodiment.

Anti-barrier cell agents can include anti-inflammatory and/or immunosuppressive mechanisms that affect the wound healing process, for example, healing of the wound created by the incision into which an implantable device is inserted. Cyclosporine, which stimulates very high levels of neovascularization around biomaterials, can be incorporated into a biointerface membrane of a preferred embodiment [see U.S. Pat. No. 5,569,462 to Martinson et al., which is incorporated herein by reference in its entirety.] Alternatively, Dexamethasone, which abates the intensity of the FBC response at the tissue-device interface, can be incorporated into a biointerface membrane of a preferred embodiment. Alternatively, Rapamycin, which is a potent specific inhibitor of some macrophage inflammatory functions, can be incorporated into a biointerface membrane of a preferred embodiment.

Other suitable medicaments, pharmaceutical compositions, therapeutic agents, or other desirable substances can be incorporated into the membranes of preferred embodiments, including, but not limited to, anti-inflammatory agents, anti-infective agents, and anesthetics.

Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetometaphen, aminosalicylic acid, aspirin, celecoxib, choline magnesium trisalicylate, diclofenac potasium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

Generally, immunosuppressive and/or immunomodulatory agents interfere directly with several key mechanisms necessary for involvement of different cellular elements in the inflammatory response. Suitable immunosuppressive and/or immunomodulatory agents include anti-proliferative, cell-cycle inhibitors, (for example, paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxy-adenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), E. coli heat-labile enterotoxin, and advanced coatings.

Generally, anti-infective agents are substances capable of acting against infection by inhibiting the spread of an infectious agent or by killing the infectious agent outright, which can serve to reduce immuno-response without inflammatory response at the implant site. Anti-infective agents include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

Vascularization Agents

Generally, vascularization agents include substances with direct or indirect angiogenic properties. In some cases, vascularization agents may additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation, however it is believed that some barrier-cell effects can result indirectly from the effects of vascularization agents.

Vascularization agents include mechanisms that promote neovascularization and accelerate wound healing around the membrane and/or minimize periods of ischemia by increasing vascularization close to the tissue-device interface. Sphingosine-1-Phosphate (S1P), which is a phospholipid possessing potent angiogenic activity, is incorporated into a biointerface membrane of a preferred embodiment. Monobutyrin, which is a potent vasodilator and angiogenic lipid product of adipocytes, is incorporated into a biointerface membrane of a preferred embodiment. In another embodiment, an anti-sense molecule (for example, thrombospondin-2 anti-sense), which increases vascularization, is incorporated into a biointerface membrane.

Vascularization agents can include mechanisms that promote inflammation, which is believed to cause accelerated neovascularization and wound healing in vivo. In one embodiment, a xenogenic carrier, for example, bovine collagen, which by its foreign nature invokes an immune response, stimulates neovascularization, and is incorporated into a biointerface membrane of the preferred embodiments. In another embodiment, Lipopolysaccharide, which is a potent immunostimulant, is incorporated into a biointerface membrane. In another embodiment, a protein, for example, a bone morphogenetic protein (BMP), which is known to modulate bone healing in tissue, is incorporated into a biointerface membrane of a preferred embodiment.

Generally, angiogenic agents are substances capable of stimulating neovascularization, which can accelerate and sustain the development of a vascularized tissue bed at the tissue-device interface. Angiogenic agents include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (for example, decorin or vimentin), glenipin, hydrogen peroxide, nicotine, and Growth Hormone.

Generally, pro-inflammatory agents are substances capable of stimulating an immune response in host tissue, which can accelerate or sustain formation of a mature vascularized tissue bed. For example, pro-inflammatory agents are generally irritants or other substances that induce chronic inflammation and chronic granular response at the wound-site. While not wishing to be bound by theory, it is believed that formation of high tissue granulation induces blood vessels, which supply an adequate, or rich supply of analytes to the device-tissue interface. Pro-inflammatory agents include, but are not limited to, xenogenic carriers, Lipopolysaccharides, S. aureus peptidoglycan, and proteins.

Other substances that can be incorporated into membranes of preferred embodiments include various pharmacological agents, excipients, and other substances well known in the art of pharmaceutical formulations.

Bioactive Agent Delivery Systems and Methods

There are a variety of systems and methods by which the bioactive agent is incorporated into the biointerface membranes of the preferred embodiments. In some embodiments, the bioactive agent is incorporated at the time of manufacture of the biointerface membrane. For example, the bioactive agent can be blended prior to curing the biointerface membrane, or subsequent to biointerface membrane manufacture, for example, by coating, imbibing, solvent-casting, or sorption of the bioactive agent into the biointerface membrane. Although the bioactive agent is preferably incorporated into the biointerface membrane, in some embodiments the bioactive agent can be administered concurrently with, prior to, or after implantation of the device systemically, for example, by oral administration, or locally, for example, by subcutaneous injection near the implantation site. A combination of bioactive agent incorporated in the biointerface membrane and bioactive agent administration locally and/or systemically can be preferred in certain embodiments.

The biointerface membranes of the preferred embodiments preferably include a bioactive agent, which is incorporated into at least one of the first and second domains of the biointerface membrane, and/or which is incorporated into the device and adapted to diffuse through the first and/or second domains, in order to modify the tissue response of the host to the membrane. In some embodiments wherein the biointerface membrane is used with an analyte-measuring device, the bioactive agent is incorporated only into a portion of the biointerface membrane adjacent to the sensing region of the device, over the entire surface of the device except over the sensing region, or any combination thereof, which can be helpful in controlling different mechanisms and/or stages of the maturation of the FBC. In some alternative embodiments however, the bioactive agent is incorporated into the implantable device proximal to the biointerface membrane, such that the bioactive agent diffuses through the biointerface membrane to the host tissue.

The bioactive agent can include a carrier matrix, wherein the matrix includes one or more of collagen, a particulate matrix, a resorbable or non-resorbable matrix, a controlled-release matrix, and/or a gel. In some embodiments, the carrier matrix includes a reservoir, wherein a bioactive agent is encapsulated within a microcapsule. The carrier matrix can include a system in which a bioactive agent is physically entrapped within a polymer network. In some embodiments, the bioactive agent is cross-linked with the biointerface membrane, while in others the bioactive agent is sorbed into the biointerface membrane, for example, by adsorption, absorption, or imbibing. The bioactive agent can be deposited in or on the biointerface membrane, for example, by coating, filling, or solvent casting. In certain embodiments, ionic and nonionic surfactants, detergents, micelles, emulsifiers, demulsifiers, stabilizers, aqueous and oleaginous carriers, solvents, preservatives, antioxidants, or buffering agents are used to incorporate the bioactive agent into the biointerface membrane. The bioactive agent can be incorporated into a polymer using techniques such as described above, and the polymer can be used to form the biointerface membrane, coatings on the biointerface membrane, portions of the biointerface membrane, and/or a portion of an implantable device.

The biointerface membrane can be manufactured using techniques known in the art. The bioactive agent can be sorbed into the biointerface membrane, for example, by soaking the biointerface membrane for a length of time (for example, from about an hour or less to about a week or more, preferably from about 4, 8, 12, 16, or 20 hours to about 1, 2, 3, 4, 5, or 7 days). Absorption of Dexamethasone into a porous silicone membrane is described in the experimental section.

The bioactive agent can be blended into uncured polymer prior to forming the biointerface membrane. The biointerface membrane is then cured and the bioactive agent thereby cross-linked and/or encapsulated within the polymer that forms the biointerface membrane. For example, Monobutyrin was covalently bonded to a silicone matrix in such a manner that is slowly cleavable under in vivo conditions. The alcohol groups of Monobutyrin react with a silanol group, resulting in a C—O—Si bond. This bond is known to be susceptible to hydrolysis, and is therefore cleaved to yield the original alcohol and silanol. Thus, the Monobutyrin is released from the silicone matrix according to the rate of hydrolysis. Other bioactive agents, such as Dexamethasone, comprise alcohol groups and can be bound to a silicone matrix in a similar manner.

In yet another embodiment, microspheres are used to encapsulate the bioactive agent. The microspheres can be formed of biodegradable polymers, most preferably synthetic polymers or natural polymers such as proteins and polysaccharides. As used herein, the term polymer is used to refer to both to synthetic polymers and proteins. U.S. Pat. No. 6,281,015, which is incorporated herein by reference in its entirety, discloses some systems and methods that can be used in conjunction with the preferred embodiments. In general, bioactive agents can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or (6) a combination thereof. Bioactive agents can be incorporated as particulates or by co-dissolving the factors with the polymer. Stabilizers can be incorporated by addition of the stabilizers to the factor solution prior to formation of the microspheres.

The bioactive agent can be incorporated into a hydrogel and coated or otherwise deposited in or on the biointerface membrane. Some hydrogels suitable for use in the preferred embodiments include cross-linked, hydrophilic, three-dimensional polymer networks that are highly permeable to the bioactive agent and are triggered to release the bioactive agent based on a stimulus.

The bioactive agent can be incorporated into the biointerface membrane by solvent casting, wherein a solution including dissolved bioactive agent is disposed on the surface of the biointerface membrane, after which the solvent is removed to form a coating on the membrane surface.

In yet another embodiment, the interconnected cavities of the biointerface membrane are filled with the bioactive agent. Preferably, a bioactive agent, with or without a carrier matrix, fills the cavities of the membrane, depending on the loading and release properties desired, which are discussed in more detail below.

The bioactive agent can be compounded into a plug of material, which is placed within the implantable device, such as is described in U.S. Pat. Nos. 4,506,680 and 5,282,844, which are incorporated herein by reference in their entirety. In contrast to the method disclosed in U.S. Pat. Nos. 4,506,680 and 5,282,844, in the preferred embodiments it is preferred to dispose the plug beneath a membrane system, for example, beneath the sensing membrane or biointerface membrane. In this way, the bioactive agent is controlled by diffusion through the membrane, which provides a mechanism for sustained-release of the bioactive agent long-term in the host.

Release of Bioactive Agents

Numerous variables can affect the pharmacokinetics of bioactive agent release. The bioactive agents of the preferred embodiments can be optimized for short- and/or long-term release. In some embodiments, the bioactive agents of the preferred embodiments are designed to aid or overcome factors associated with short-term effects (for example, acute inflammation) of the foreign body response, which can begin as early as the time of implantation and extend up to about one month after implantation. In some embodiments, the bioactive agents of the preferred embodiments are designed to aid or overcome factors associated with long-term effects, for example, chronic inflammation, barrier cell layer formation, or build-up of fibrotic tissue of the foreign body response, which can begin as early as about one week after implantation and extend for the life of the implant, for example, months to years. In some embodiments, the bioactive agents of the preferred embodiments combine short- and long-term release to exploit the benefits of both.

As used herein, "controlled," "sustained," or "extended" release of the factors can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

Short-term release of the bioactive agent in the preferred embodiments generally refers to release over a period of from about 1 day or less to about 2, 3, 4, 5, 6, or 7 days, 2 or 3 weeks, 1 month, or more. More preferably, the short-term release of the bioactive agents occurs over from about 14, 15, 16, 17, or 18 days up to about 19, 20, or 21 days.

Conventional devices, such as implantable analyte measuring-devices, drug delivery devices, and cell transplantation devices that require transport of solutes across the device-tissue interface for proper function, tend to lose their function after the first few days following implantation. At least one reason for this loss of function is the lack of direct contact with circulating fluid for appropriate analyte transport to the device. Therefore, in some embodiments, short-term release of certain bioactive agents, for example vascularization agents, can increase the circulating fluid to the device for an extended period of time.

Additionally, it is believed that short-term release of the bioactive agent can have a positive effect of the functionality of porous biointerface membranes during the initial tissue ingrowth period prior to formation of a capillary bed. For example, when a device requiring analyte transport across its device-tissue interface is implanted, a "sleep period" can occur which begins as early as the first day after implantation and extends as far as one month after implantation. However shorter sleep periods are more common. During this sleep period, extensive ingrowth of tissue into the porous structure causes the inflammatory cells responsible for facilitating wound healing to proliferate within the local environment of the wound region. Because these cells are respiring, they consume some or all of the glucose and oxygen that is within the wound environment, which has shown to block adequate flow of analytes to the implantable device. Accordingly in some embodiments, it is believed that short-term release of certain bioactive agents, for example vascularization agents, can aid in providing adequate vascularization to substantially overcome the effects of the sleep period, and thereby allow sufficient analytes to pass through to the implantable device.

Additionally, it is believed that short-term release of the bioactive agent can have an enhanced effect on neovascularization at the tissue-device interface. Although neovascularization alone is generally not sufficient to provide sufficient analyte transport at the device-tissue interface, in combination with other mechanisms, enhanced neovascularization can result in enhanced transport of analytes from the host to the implanted device. Therefore in some embodiments, short-term release of certain bioactive agents, for example angiogenic agents, can have a positive effect on neovascularization and thereby enhance transport of analytes at the device-tissue interface.

Additionally, it is believed that short-term release of the bioactive agent can be sufficient to reduce or prevent barrier cell layer formation. Formation of a cohesive monolayer of closely opposed cells, e.g., macrophages and foreign body giant cells, interfere with the transport of analytes across the tissue-device interface, also known as a barrier cell layer, and are large contributors to poor device performance. See U.S. Pat. No. 6,702,857, which is incorporated herein by reference in its entirety. Therefore in some embodiments, it is believed that short-term release of certain bioactive agents, for example, anti-barrier cell agents, can aid in preventing barrier cell layer formation.

Additionally, it is believed that short-term release of the bioactive agent can be sufficient to prevent negative effects of acute inflammation caused, for example, by surgical trauma, micro-motion, or macro-motion of the device in the soft tissue. Short-term release of anti-inflammatory agents can be sufficient to rescue a biointerface membrane from the negative effects associated with such acute inflammation, rendering adequate analyte transport.

Long-term release of the bioactive agent in the preferred embodiments generally occurs over a period of from about 1 month to about 2 years or more, preferably from at least about 2 months to at least about 13, 14, 15, 16, 17, 18, 19, 20, 21, 22, or 23 months, and more preferably from at least about 3 months to at least about 4, 5, 6, 7, 8, 9, 10, 11, or 12 months.

Long-term glucose-measuring device experiments demonstrate that many biointerface materials experience a distinct and continual decline in sensitivity, for example, reduced analyte transport, beginning at three months after implantation in some cases. It is believed that this decline in analyte transport can be a result of barrier cell layer formation, cellular growth at the membrane, and/or thickening of the fibrous elements of the foreign body capsule. Other contributing factors can include chronic inflammation, which is believed to be due to micro-motion or macro-motion of the device; delamination of the biointerface membrane, which is believed to be due to cellular ingrowth within and under the biointerface membrane; compression of the biointerface membrane due to increasing compression of the foreign body capsule around the device; and distortion of the biointerface membrane, which is believed to be a result of a combination of compression and cellular ingrowth, for example.

Accordingly, long-term release of certain bioactive agents can modulate the foreign body response sufficiently to prevent long-term thickening of the foreign body capsule, reduce or prevent barrier cell layer formation, reduce or prevent chronic inflammation, reduce or prevent extensive cellular ingrowth, and/or reduce or prevent compression of the foreign body capsule on the biointerface membrane.

Loading of Bioactive Agents

The amount of loading of the bioactive agent into the biointerface membrane can depend upon several factors. For example, the bioactive agent dosage and duration can vary with the intended use of the biointerface membrane, for example, cell transplantation, analyte measuring-device, and the like; differences among patients in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above.

In some embodiments, wherein the bioactive agent is incorporated into the biointerface membrane without a carrier matrix, the preferred level of loading of the bioactive agent into the biointerface membrane can vary depending upon the nature of the bioactive agent. The level of loading of the bioactive agent is preferably sufficiently high such that a biological effect is observed. Above this threshold, bioactive agent can be loaded into the biointerface membrane so as to imbibe up to 100% of the solid portions, cover all accessible surfaces of the membrane, and/or fill up to 100% of the accessible cavity space. Typically, the level of loading (based on the weight of bioactive agent(s), biointerface membrane, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably form about 2, 3, 4, 5, 6, 7, 8, 9, 10, 15, or 20 wt. % up to about 25, 30, 35, 40, or 45 wt. %.

When the bioactive agent is incorporated into the biointerface membrane with a carrier matrix, such as a gel, the gel concentration can be optimized, for example, loaded with one or more test loadings of the bioactive agent. It is generally preferred that the gel contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive can also be incorporated into the matrix.

Referring now to microencapsulated bioactive agents, the release of the agents from these polymeric systems generally occur by two different mechanisms. The bioactive agent can be released by diffusion through aqueous filled channels generated in the dosage form by the dissolution of the agent or by voids created by the removal of the polymer solvent or a pore forming agent during the original micro-encapsulation. Alternatively, release can be enhanced due to the degradation of the polymer. With time, the polymer erodes and generates increased porosity and microstructure within the device. This creates additional pathways for release of the bioactive agent.

Implantable Devices

Biointerface membranes of the preferred embodiments are suitable for use with implantable devices in contact with a biological fluid. For example, the biointerface membranes can be utilized with implantable devices and methods for monitoring and determining analyte levels in a biological fluid, such as measurement of glucose levels for individuals having diabetes. In some embodiments, the analyte-measuring device is a continuous device. Alternatively, the device can analyze a plurality of intermittent biological samples. The analyte-measuring device can use any method of analyte-measurement, including enzymatic, chemical, physical, electrochemical, spectrophotometric, polarimetric, calorimetric, radiometric, or the like.

Although some of the description that follows is directed at glucose-measuring devices, including the described biointerface membranes and methods for their use, these biointerface membranes are not limited to use in devices that measure or monitor glucose. These biointerface membranes are suitable for use in a variety of devices, including, for example, those that detect and quantify other analytes present in biological fluids (including, but not limited to, cholesterol, amino acids, and lactate), cell transplantation devices (see, e.g., U.S. Pat. Nos. 6,015,572, 5,964,745, and 6,083,523), drug delivery devices (see, e.g., U.S. Pat. Nos. 5,458,631, 5,820,589, and 5,972,369) and electrical delivery and/or measuring devices such as implantable pulse generation cardiac pacing devices (see, e.g., U.S. Pat. Nos. 6,157,860, 5,782,880, and 5,207,218), electrocardiogram devices (see, e.g., U.S. Pat. Nos. 4,625,730 and 5,987,352) electrical nerve stimulating devices (see, e.g., U.S. Pat. Nos. 6,175,767, 6,055,456, and 4,940,065), and in combination with angiogenic factor gene transfer technology to enhance implantable device function (see, e.g., Klueh U, Dorsky D I, Kreutzer D L. Use of vascular endothelial cell growth factor gene transfer to enhance implantable device function in vivo. *J Biomed Mater Res.* 2003 Dec. 15; 67A(4):1072-86), to name but a few The biointerface membranes can be utilized in conjunction with transplanted cells, for example, transplanted genetic engineered cells of Langerhans, either allo, auto or xeno geneic in origin, as pancreatic beta cells to increase the diffusion of nutrients to the islets, but additionally utilizing a biointerface membrane of the preferred embodiment on a measuring-device proximal to the transplanted cells to sense glucose in the tissues of the patient to monitor the viability of the implanted cells. Preferably, implantable devices that include the biointerface membranes of the preferred embodiments are implanted in soft tissue, for example, abdominal, subcutaneous, and peritoneal tissues, the brain, the intramedullary space, and other suitable organs or body tissues.

In addition to the glucose-measuring device described below, the biointerface membranes of the preferred embodiments can be employed with a variety of known continuous glucose measuring-devices. For example, the biointerface membrane can be employed in conjunction with a continuous glucose measuring-device that comprises a subcutaneous measuring-device such as is described in U.S. Pat. No. 6,579,690 to Bonnecaze et al. and U.S. Pat. No. 6,484,046 to Say et al. In another alternative embodiment, the continuous glucose measuring-device comprises a refillable subcutaneous measuring-device such as is described in U.S. Pat. No. 6,512,939 to Colvin et al. All of the above patents are incorporated in their entirety herein by reference. In general, it is understood that the disclosed embodiments are applicable to a variety of continuous glucose measuring-device configurations.

Implantable devices for detecting the presence of an analyte or analyte concentrations in a biological system can utilize the biointerface membranes of the preferred embodiments to increase local vascularization and interfere with the formation of a barrier cell layer, thereby assuring that the measuring-device receives analyte concentrations representative of that in the vasculature. Drug delivery devices can utilize the biointerface membranes of the preferred embodiments to protect the drug housed within the device from host inflammatory or immune cells that might potentially damage or destroy the drug. In addition, the biointerface membrane can prevent or hinder the formation of a barrier cell layer that can interfere with proper dispensing of drug from the device for treatment of the host. Correspondingly, cell transplantation devices can utilize the biointerface membranes of the preferred embodiments to protect the transplanted cells from attack by the host inflammatory or immune response cells while simultaneously preventing the formation of a barrier cell layer, thereby permitting nutrients as well as other biologically active molecules needed by the cells for survival to diffuse through the membrane.

Figure 3:
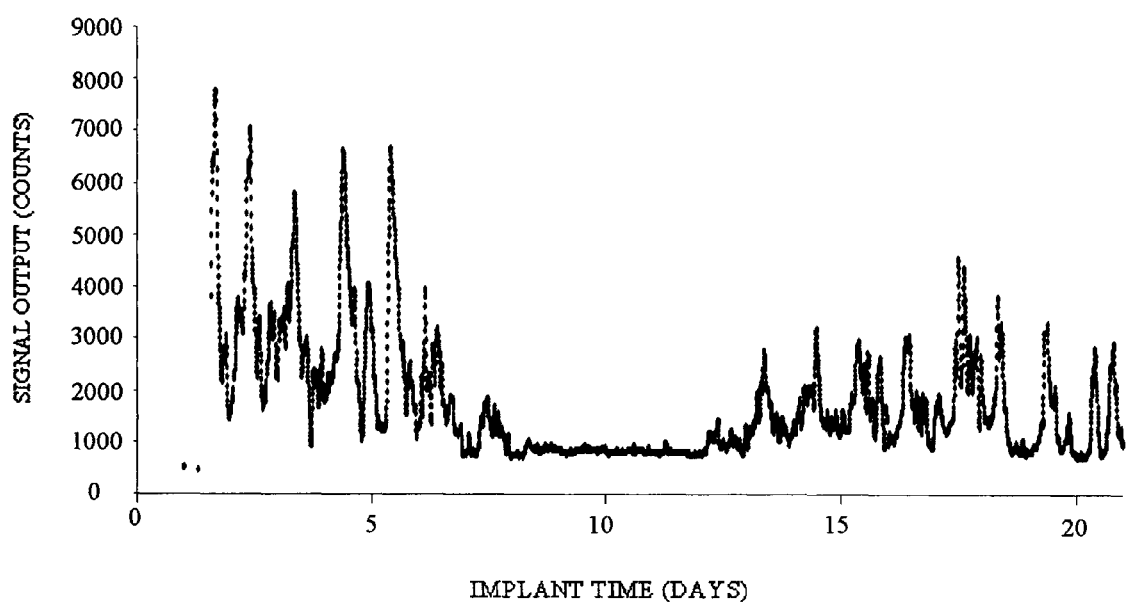
FIG. 3 is a graph of sensor output from a glucose sensor implanted in a human, showing the raw data signal from the sensor from time of implant up to about 21 days after implant.

FIG. 3 is a graph of signal output from a glucose-measuring device implanted in a human, wherein the device included a biointerface membrane without a bioactive agent incorporated therein. The graph shows the data signal produced by the device from time of implant up to about 21 days after implant. The x-axis represents time in days; the y-axis presents the data signal from the device output in counts. The term "counts," as used herein, is a broad term and is used in its ordinary sense, including, without limitation, a unit of measurement of a digital signal. In one example, a raw data signal measured in counts is directly related to a voltage (converted by an A/D converter), which is directly related to current. The glucose-measuring device of this experiment is described in more detail with reference to FIGS. 4A and 4B.

Referring to FIG. 3, the device associated with the signal output was implanted during day 1. The associated signal output is shown beginning at day 1 and substantially tracks the rise and fall of the patient's glucose levels during the first few days after implant. It is noted that approximately 5 days after device implant, the signal output experienced a temporary decrease in sensitivity, sometimes referred to as a "sleep period." It is believed that this loss in sensitivity is due to migration of cells, which consume glucose and oxygen during formation of a vascularized foreign body capsule (tissue bed) into and around the biointerface membrane. In this example, the sleep period continues for approximately 7 days during which time the glucose-measuring device does not accurately track the patient's glucose levels. Approximately 12 days after implant, the signal output resumes function, as indicated by the rise and fall of the signal output, which correlates with the rise and fall the patient's glucose levels. It is believed that this resuming of signal output correlates with a reduction in the numbers of inflammatory cells and a mature vascularized tissue bed within and around the biointerface membrane that allows glucose and oxygen to transport through the biointerface membrane to the glucose-measuring device. The difference in sensitivity of the device before and after the sleep period is attributed to the effect of the vascularized tissue bed on the transport of glucose and oxygen therethrough. In summary, it has been shown that the an implantable device with a biointerface membrane but without a bioactive agent incorporated therein sometimes undergoes a sleep period in the device during the formation of the vascularized tissue bed and/or a foreign body capsule surrounding and within the implant.

In order to overcome the sleep period described above, it is believed that by incorporating bioactive agents that enhance local vascularization and inhibit inflammatory cells within or around the biointerface membranes of the preferred embodiments on implanted devices, accelerated maturation of a vascularized tissue bed and decreased inflammatory response will occur, which increases the rate at which devices become functional, reducing or eliminating the loss insensitivity seen in the experiment above. The bioactive agents that are incorporated into the biointerface membrane 30 used on implantable devices of certain preferred embodiments are chosen to optimize the rate of biointerface formation.

In some embodiments, the bioactive agents that are incorporated into the biointerface membrane 30 used on implantable devices are chosen to optimize reliable biointerface formation. In some situations, stable device function does not occur due to faulty surgical techniques, acute or chronic movement of the implant, or other surgery-, patient-, or implantation site-related complications, which can create acute and/or chronic inflammation at the implant site and subsequent formation of barrier cell layer and/or thick fibrotic tissue build-up. While not wishing to be bound by theory, it is believed that bioactive agents described in the preferred embodiments, for example anti-inflammatory agents and/or anti-barrier cell agents, can provide sufficient biological activity to reduce the effects of site-related complications, and thereby increase reliability of device functionality.

In some embodiments, the bioactive agents that are incorporated into the biointerface membrane 30 used on implantable devices are chosen to optimize the stability of the biointerface. Even after devices have been implanted for some length of time and begin to function, it is observed that device stability can be lost gradually or suddenly. It is believed that this loss of stability or function can be attributed the biointerface, based on post-explantation histological examinations. This conclusion is further supported by the observation that devices typically function in vitro after removal from animals or humans. It is therefore believed that delivery of bioactive agents described in the preferred embodiments can increase the stability of the biointerface so that device calibration values remain sufficiently stable so as to provide accurate measurements.

Figure 4A:
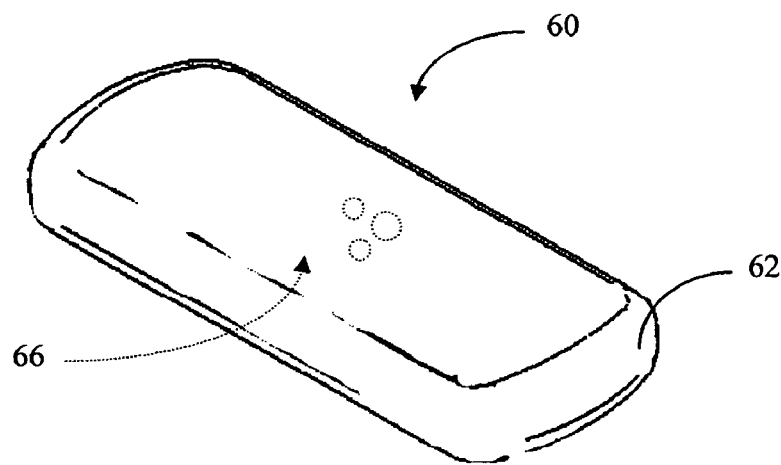
FIG. 4A is a perspective view of an assembled glucose-measuring device, including sensing and biointerface membranes incorporated thereon.
Figure 4B:
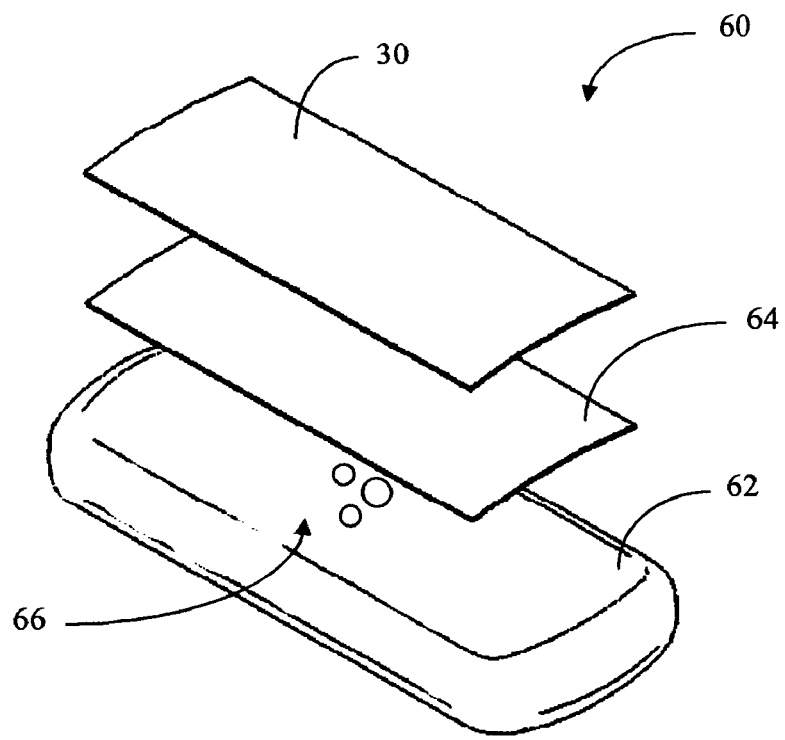
FIG. 4B is an exploded perspective view of the glucose-measuring device of FIG. 4A, showing the sensing membrane and the biointerface membrane.

FIGS. 4A and 4B are perspective views of an implantable glucose measuring-device of a preferred embodiment. FIG. 4A is a view of the assembled glucose measuring-device, including sensing and biointerface membranes incorporated thereon. FIG. 4B is an exploded view of the glucose measuring-device 60, showing the body 62, the sensing membrane 64, and the biointerface membrane 30 of a preferred embodiment, such as is described in more detail above.

The body 62 is preferably formed from epoxy molded around the measuring-device electronics (not shown), however the body can be formed from a variety of materials, including metals, ceramics, plastics, or composites thereof. Co-pending U.S. patent application Ser. No. 10/646,333, entitled, "Optimized Device Geometry for an Implantable Glucose Device" discloses suitable configurations suitable for the body 62, and is incorporated by reference in its entirety.

In one preferred embodiment, the measuring-device 60 is an enzyme-based measuring-device, which includes an electrode system 66 (for example, a platinum working electrode, a platinum counter electrode, and a silver/silver chloride reference electrode), which is described in more detail with reference to U.S. patent application Ser. No. 09/916,711, entitled "Sensor head for use with implantable devices," which is incorporated herein by reference in its entirety. However, a variety of electrode materials and configurations can be used with the implantable glucose measuring-devices of the preferred embodiments. The top ends of the electrodes are in contact with an electrolyte phase (not shown), which is a free-flowing fluid phase disposed between a sensing membrane 64 and the electrode system 66. In this embodiment, the counter electrode is provided to balance the current generated by the species being measured at the working electrode. In the case of a glucose oxidase based glucose measuring-device, the species measured at the working electrode is $H_2O_2$. Glucose oxidase catalyzes the conversion of oxygen and glucose to hydrogen peroxide and gluconate according to the following reaction:

$$Glucose+O_2 \rightarrow Gluconate+H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons ($2H^+$), two electrons ($2e^-$), and one oxygen molecule ($O_2$).

In this embodiment, a potentiostat is employed to monitor the electrochemical reaction at the electroactive surface(s). The potentiostat applies a constant potential to the working and reference electrodes to determine a current value. The current that is produced at the working electrode (and flows through the circuitry to the counter electrode) is substantially proportional to the amount of $H_2O_2$ that diffuses to the working electrode. Accordingly, a raw signal can be produced that is representative of the concentration of glucose in the user's body, and therefore can be utilized to estimate a meaningful glucose concentration.

In some embodiments, the sensing membrane 64 includes an enzyme, for example, glucose oxidase, and covers the electrolyte phase. The sensing membrane 64 preferably includes a resistance domain most distal from the electrochemically reactive surfaces, an enzyme domain less distal from the electrochemically reactive surfaces than the resistance domain, and an electrolyte domain adjacent to the electrochemically reactive surfaces. However, it is understood that a sensing membrane 64 modified for other devices, for example, by including fewer or additional domains, is within the scope of the preferred embodiments. Co-pending U.S. patent application Ser. No. 10/838,912 filed May 3, 2004 entitled, "IMPLANTABLE ANALYTE SENSOR," and U.S. patent application Ser. No. 09/916,711, entitled, "SENSOR HEAD FOR USE WITH IMPLANTABLE DEVICES," each of which are incorporated herein by reference in their entirety, describes membranes that can be used in some embodiments of the sensing membrane 64. In some embodiments, the sensing membrane 64 can additionally include an interference domain that blocks some interfering species; such as described in the above-cited co-pending patent application. Co-pending U.S. patent application Ser. No. 10/695,636, entitled, "SILICONE COMPOSITION FOR BIOCOMPATIBLE MEMBRANE" also describes membranes that can be used for the sensing membrane 64 of the preferred embodiments, and is incorporated herein by reference in its entirety.

The biointerface membrane 30 includes a biointerface membrane of a preferred embodiment, which covers the sensing membrane and supports tissue ingrowth, interferes with the formation of a barrier cell layer, and protects the sensitive regions of the measuring-device 60 from host inflammatory response. Preferably, the biointerface membrane 30 is a formed from a non-resorbable membrane and includes a porous architecture with a bioactive agent incorporated therein.

The biointerface membranes of the preferred embodiments can incorporate a variety of mechanisms, including materials, architecture, cavity size, and incorporation of one or bioactive agents, which can be function alone or in combination to enhance wound healing, which when incorporated into an analyte measuring-device, result in enhanced device performance.

In one embodiment, an anchoring material (not shown) is formed substantially around the device body in order to stabilize the device in vivo. Controlled release of a bioactive agent from the biointerface membrane 30, such as an anti-inflammatory agent, is provided for a period of time up to about one month, which is believed to be sufficient to reduce the effects of tissue trauma at the device interface prior to stabilization of the device in vivo. Consequently, when the device is stable (for example, when sufficient tissue ingrowth into the anchoring material occurs to ensure minimal motion and less broken fat cells, seepage and other inflammatory factors), it is safe to permit the biointerface to heal with good vascularization.

EXPERIMENTS

The following examples serve to illustrate certain preferred embodiments and aspects and are not to be construed as limiting the scope thereof.

In the preceding description and the experimental disclosure which follows, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Example 1

Preparation of Biointerface Membrane with Porous Silicone

A porous silicone cell disruptive (first) domain was prepared by mixing approximately 1 kg of sugar crystals with approximately 36 grams of water for 3-6 minutes. The mixture was then pressed into a mold and baked at 80° C. for 2 hours. The silicone was vacuumed into the mold for 6 minutes and cured at 80° C. for at least 2 hours. The sugar was dissolved using heat and deionized water, resulting in a flat sheet, porous membrane. Different architectures were obtained by varying the crystal size (crystals having an average diameter of about 90, 106, 150, 180, and 220 μm) and distribution within the mold that the silicone was cast from. After removal of silicone from the mold, the resulting membranes were measured for material thickness.

The cell-impermeable (second) domain was prepared by placing approximately 706 gm of dimethylacetamide (DMAC) into a 3 L stainless steel bowl to which a polycarbonate urethane solution (1325 g, CHRONOFLEX™ AR 25% solids in DMAC and a viscosity of 5100 cp) and polyvinylpyrrolidone (125 g, PLASDONE™ K-90D) were added. The bowl was then fitted to a planetary mixer with a paddle type blade and the contents were stirred for one hour at room temperature. The cell-impermeable domain coating solution was then coated onto a PET release liner (Douglas Hansen Co., Inc. (Minneapolis, Minn.)) using a knife over roll set at a 0.012" (305 μm) gap. This film was then dried at 305° F. (152° C.). The final film was approximately 0.0015" (38 μm) thick. The biointerface membrane was prepared by pressing the porous silicone onto the cast cell-impermeable domain.

The advantages of using porous silicone included the mechanical robustness of the material, the ability to mold it into various structural architectures, the ability to load lipid-soluble bioactive agents into the membrane without a carrier, the ability to fill the large pores of the material with collagen-coupled bioactive agents, and the high oxygen solubility of silicone that allowed the membrane to act as an oxygen antenna domain.

Various bioactive agents can be incorporated into the biomaterials of preferred embodiments. In some embodiments, such bioactive agent containing biomaterials can be employed in an implantable glucose device for various purposes, such as extending the life of the device or to facilitate short-term function. The following experiments were performed with a porous silicone biointerface membrane prepared as described above, in combination with bioactive agents, for the purpose of accelerated device initiation and long-term sustentation.

Example 2

Neovascularizing Agents in Biointerface Membranes

In a first experiment, disks were employed, which were prepared for three-week implantation into the subcutaneous space of rats to test a neovascularizing agent. Monobutyrin was chosen based on its hydrophobic characteristics and ability to promote neovascularization. This experiment consisted of soaking the porous silicone prepared as described above in the concentrated solution of the bioactive compound at elevated temperature. This facilitated a partitioning of the agent into the porous silicone dependent upon its solubility in silicone rubber. Porous silicone disks were exposed to phosphate buffer mixed with Monobutyrin (500 mg/ml) for four days at 47° C. These disks were then autoclaved in the same solution, then rinsed in sterile saline immediately prior to implant. Disks were implanted into the subcutaneous dorsal space. Rats were euthanized and disks explanted at 3 weeks. Disks were fixed in 10% NBF and histologically processed and analyzed. The numbers of vessels per high power field were evaluated from porous silicone disks embedded with and without Monobutyrin after 3 weeks of implantation.

Figure 5:
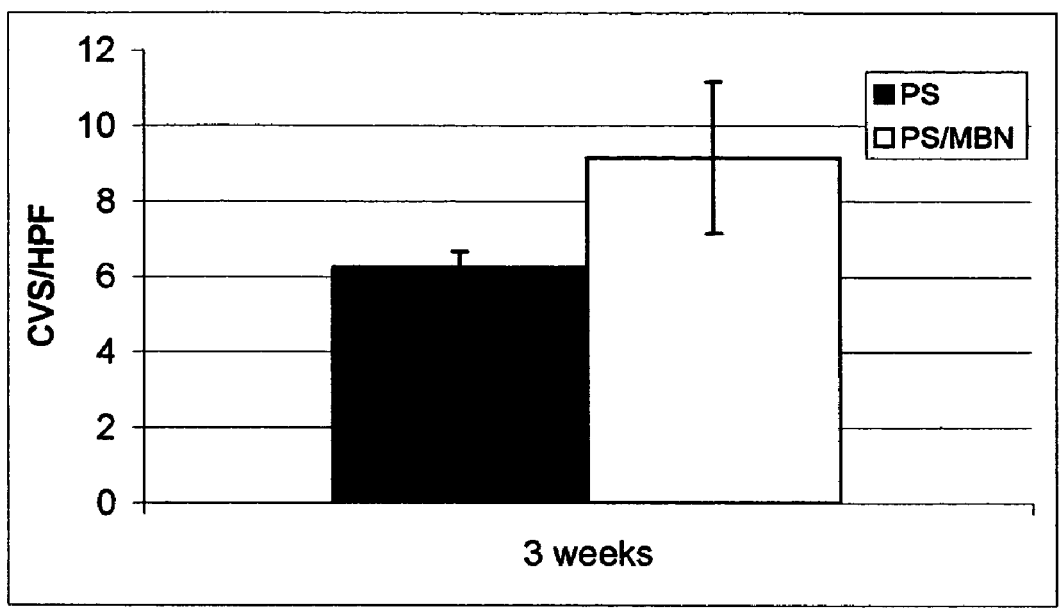
FIG. 5 is a bar graph that shows average number of vessels (per high-powered field of vision) of porous silicone materials embedded with Monobutyrin after three weeks of implantation.

FIG. 5 is a bar graph that shows average number of vessels (per high-powered field of vision) of porous silicone (PS) materials embedded with and without Monobutyrin (MBN) after three weeks of implantation. MBN was chosen because of its reported neovascularizing properties. See Halvorsen et al., *J. Clin. Invest.* 92(6):2872-6 (1993); Dobson et al., *Cel* 61(2)l (1990); and English et al., *Cardiovasc. Res* 49(3):588-99. (2001). An overall increase in the numbers of vessels per high power field was seen with MBN as compared to porous silicone alone (p<0.05). These preliminary data suggested that bioactive agents absorbed into porous silicone can alter healing in the first month. It is believed that this increase in vessels results in improved device performance.

Example 3

Anti-Inflammatory Agents in Biointerface Membranes

Dexamethasone was loaded into a porous silicone biointerface membrane by sorption. In this experiment, 100 mg of Dexamethasone was mixed with 10 mL of Butanone (solvent) and the mixture heated to about 70° C.-80° C. to dissolve the Dexamethasone in the solvent. The solution was then centrifuged to ensure solubility. The supernatant was pipetted from the solution and placed in a clean glass vial. Disks of porous silicone were placed in the Dexamethasone solution at 40° C. for 5 days, after which the disks were air-dried. The disks were sprayed with 70% isopropanol to remove trapped air from the porous silicone, attached to glucose sensors, and sterilized in 0.5% glutaraldehyde for 24 hours. After rinsing, the glucose sensors were placed in a 40 mL phosphate buffer solution conical. These conicals were placed on a shaker table with a setting of about 7 or 8. Dexamethasone release in PBS solution was measured daily for the first five days and then every three days until the end of the experiment using a UV spectrometer. After each measurement when the absorbance was above 0.1, the PBS solution was changed to ensure that it did no reach its maximum solubility). The release kinetics are graphed on FIG. 6.

Figure 6:
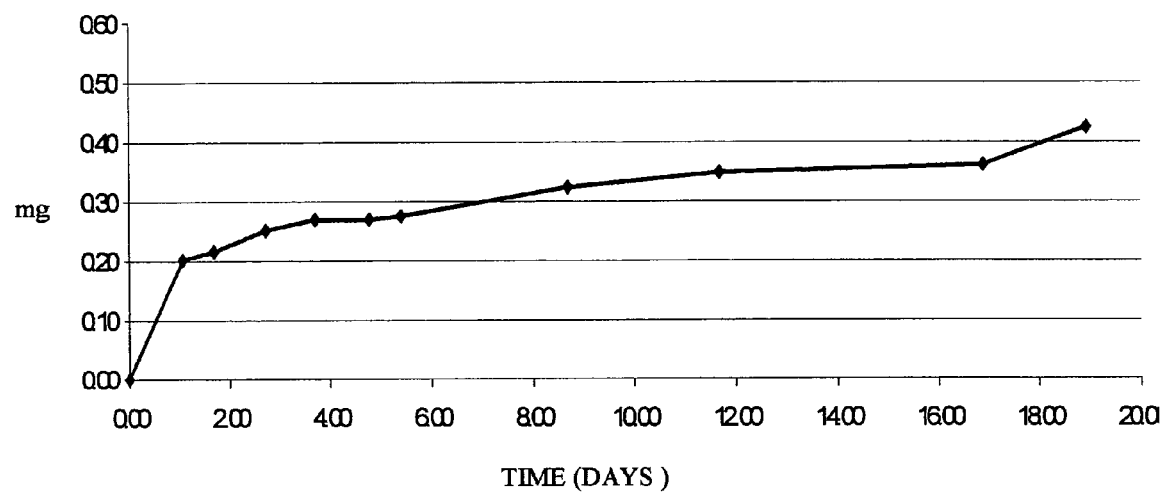
FIG. 6 is a graph that shows release kinetics over time in PBS solution for porous silicone with Dexamethasone incorporated therein.

FIG. 6 is a graph that shows the cumulative amount of Dexamethasone released over time as described above. Namely, during the first 19 days, about 0.4 mg of Dexamethasone was released in PBS solution. The amount of Dexamethasone released is at least partially dependent upon the surface area of the biointerface membrane, including throughout the cavities of the cell disruptive domain. While not wishing to be bound by theory, it is believed that Dexamethasone released over time can modify a tissue response to the biointerface membrane in vivo, thereby substantially overcoming the effects of a "sleep period", 2) aid in preventing barrier cell layer formation, and/or 3) rescuing a biointerface membrane from the negative effects associated with such acute inflammation, rendering adequate analyte transport to an implantable device.

Methods and devices that are suitable for use in conjunction with aspects of the preferred embodiments are disclosed in copending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR BIOCOMPATIBLE MEMBRANE"; U.S. application Ser. No. 10/648,849 filed Aug. 22, 2003 and entitled, "SYSTEMS AND METHODS FOR REPLACING SIGNAL ARTIFACTS IN A GLUCOSE DEVICE DATA STREAM"; U.S. application Ser. No. 10/646,333 filed Aug. 22, 2003 entitled, "OPTIMIZED DEVICE GEOMETRY FOR AN IMPLANTABLE GLUCOSE DEVICE"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE MEASURING-DEVICE DATA"; U.S. application Ser. No. 09/916,386 filed Jul. 27, 2001 and entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE DEVICES"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE."

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. All patents, applications, and other references cited herein are hereby incorporated by reference in their entirety.

What is claimed is:

1. An implantable glucose sensor having a biointerface membrane comprising:

a first domain comprising a nonresorbable solid portion comprising a plurality of interconnected cavities having a pore size greater than about 30 μm, as determined by a bubble point test measurement, wherein the solid portion is adapted to support a tissue ingrowth in vivo;

a second domain located adjacent to the first domain, wherein the second domain is impermeable to cells or cell processes and is configured to allow a passage of glucose therethrough; and a bioactive agent incorporated into the biointerface membrane, wherein the bioactive agent is capable of modifying a tissue response in such a way that sleep period effects on the implantable glucose sensor are reduced, wherein the bioactive agent is configured to be released from the first domain and/or the second domain.

2. The implantable glucose sensor according to claim 1, wherein the interconnected cavities and the solid portion are configured to redirect a fibrous tissue contracture in vivo, thereby interfering with formation of a barrier cell layer within or around the membrane.

3. The implantable glucose sensor according to claim 2, wherein the membrane comprises a micro-architecture situated within at least some of the cavities of a macro-architecture, wherein the macro-architecture comprises a frame comprising a plurality of elongated strands of a material, wherein the strands are less than about 6 μm in all but the longest dimension.

4. The implantable glucose sensor according to claim 1, wherein the solid portion is selected from the group consisting of silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene, polyvinyl alcohol, polyvinylchloride, polyvinylidene fluoride, polybutylene terephthalate, polymethylmethacrylate, polyether ether ketone, polyurethanes, cellulosic polymers, polysulfones, block copolymers thereof, and combinations or mixtures thereof.

5. The implantable glucose sensor according to claim 1, wherein the solid portion comprises silicone.

6. The implantable glucose sensor according to claim 1, wherein the bioactive agent is selected from the group consisting of inflammatory agents, growth factors, angiogenic factors, cytotoxic agents, and combinations or mixtures thereof.

7. The implantable glucose sensor according to claim 1, wherein the bioactive agent comprises a vascularization agent.

8. The implantable glucose sensor according to claim 7, wherein the vascularization agent comprises an angiogenic agent configured for stimulating a neovascularization.

9. The implantable glucose sensor according to claim 7, wherein the vascularization agent comprises sphingosine-1-phosphate.

10. The implantable glucose sensor according to claim 7, wherein the vascularization agent comprises monobutyrin.

11. The implantable glucose sensor according to claim 7, wherein the vascularization agent comprises an anti-sense molecule.

12. The implantable glucose sensor according to claim 7, wherein the vascularization agent comprises a pro-inflammatory agent configured for promoting an inflammation response or an immune response.

13. The implantable glucose sensor according to claim 12, wherein the pro-inflammatory agent comprises a xenogenic carrier.

14. The implantable glucose sensor according to claim 12, wherein the pro-inflammatory agent comprises a lipopolysaccharide (LPS).

15. The implantable glucose sensor according to claim 12, wherein the pro-inflammatory agent comprises a protein.

16. The implantable glucose sensor according to claim 7, wherein the vascularization agent is selected from the group consisting of basic fibroblast growth factor (bFGF), acidic fibroblast growth factor (aFGF), vascular endothelial growth factor (VEGF), platelet derived endothelial cell growth factor BB (PDECGF-BB), transforming growth factor beta (TGF-β), tumor necrosis factor alpha (TNF-α), and combinations or mixtures thereof.

17. The implantable glucose sensor according to claim 1, wherein the bioactive agent is incorporated into the biointerface membrane via a carrier matrix.

18. The implantable glucose sensor according to claim 17, wherein the carrier matrix is selected from the group consisting of collagen, a particulate matrix, a non-resorbable matrix, resorbable matrix, a controlled-release matrix, a gel, and combinations or mixtures thereof.

19. The implantable glucose sensor according to claim 1, wherein the bioactive agent is cross-linked with a material that forms the biointerface membrane.

20. The implantable glucose sensor according to claim 1, wherein the bioactive agent is sorbed into the biointerface membrane by a process selected from the group consisting of absorption, adsorption, imbibing, and combinations thereof.

21. The implantable glucose sensor according to claim 1, wherein the bioactive agent is configured to be released for a time period of from about one day to about one year.

22. The implantable glucose sensor according to claim 1, wherein the bioactive agent is configured to be released for a time period of from about one week to about four weeks.

23. The implantable glucose sensor according to claim 1, wherein the substantial number of each of the interconnected cavities are from about 30 μm to about 1000 μm in at least one dimension.

24. The implantable glucose sensor according to claim 1, wherein the bioactive agent is capable of modify the tissue response in such a way that maturation of a vascularized tissue bed is accelerated.

25. An implantable glucose sensor having a biointerface membrane comprising:

a first domain comprising a nonresorbable solid portion comprising a plurality of interconnected cavities having a pore size greater than about 30 μm, as determined by a bubble point test measurement, wherein the solid portion is adapted to support a tissue ingrowth in vivo;

a second domain located adjacent to the first domain, wherein the second domain is impermeable to cells or cell processes and is configured to allow a passage of glucose therethrough; and a pro-inflammatory agent incorporated into the biointerface membrane, wherein the pro-inflammatory agent is capable of modifying a tissue response in such a way that sleep period effects on the implantable glucose sensor are reduced, wherein the pro-inflammatory agent is configured to be released from the first domain and/or the second domain.

* * * * *

UNITED STATES PATENT AND TRADEMARK OFFICE
CERTIFICATE OF CORRECTION

PATENT NO. : 7,875,293 B2
APPLICATION NO. : 10/842716
DATED : January 25, 2011
INVENTOR(S) : Shults et al.

It is certified that error appears in the above-identified patent and that said Letters Patent is hereby corrected as shown below:

| Issued Patent | | Description of Discrepancy |
|---|---|---|
| Column | Line | |
| (Item 56) Page 5 Col. 1 | 63 | Under Other Publications, change "Voltammetryand" to --Voltammetry and--. |
| (Item 56) Page 5 Col. 2 | 62 | Under Other Publications, change "Aniodic" to --Anodic--. |
| (Item 56) Page 7 Col. 1 | 37 | Under Other Publications, change "wtih" to --with--. |
| (Item 56) Page 7 Col. 2 | 37 | Under Other Publications, change "pancrease" to --pancreas--. |
| (Item 56) Page 8 Col. 1 | 23 | Under Other Publications, change "Senso" to --Sensor--. |
| (Item 56) Page 8 Col. 2 | 19 | Under Other Publications, change "Membran," to --Membrane,--. |
| 4 | 58 | Change "xenogenic" to --xenogeneic--. |
| 8 | 64 | Change "andrenostenedione;" to --androstenedione;--. |
| 9 | 11 | Change "diptheria/" to --diphtheria/--. |
| 9 | 18 | Change "perioxidase;" to --peroxidase;--. |
| 9 | 27 | Change "sissomicin;" to --sisomicin;--. |
| 9 | 31-32 | Change "duodenalisa," to --duodenalis,--. |
| 9 | 39 | Change "Trepenoma pallidium," to --Treponema palladium,--. |

Signed and Sealed this
Eleventh Day of October, 2011

David J. Kappos
*Director of the United States Patent and Trademark Office*

CERTIFICATE OF CORRECTION (continued)
U.S. Pat. No. 7,875,293 B2

| | | |
|---|---|---|
| 9 | 40 | Change "stomatis" to --stomatitis--. |
| 9 | 61 | Change "(barbituates," to --(barbiturates,--. |
| 11 | 5 | Change "byproduct." to --byproduct,--. |
| 18 | 4 | Change "form" to --from--. |
| 18 | 66-67 | Change "hydroxyethylmetharcrylate, hydroxyapeptite," to --hydroxyethylmethacrylate, hydroxyapatite,--. |
| 19 | 2 | Change "nintinol," to --nitinol,--. |
| 22 | 47 | Change "potasium," to --potassium,--. |
| 22 | 52 | Change "melenamic" to --mefenamic--. |
| 22 | 56 | Change "betamethesone," to --betamethasone,--. |
| 23 | 3 | Change "infiximab)," to --infliximab),--. |
| 23 | 5 | Change "methothrexate," to --methotrexate,--. |
| 23 | 6 | Change "vincristing, mitomycine," to --vincristine, mitomycin,--. |
| 23 | 21 | Change "aminoclycosides" to --aminoglycosides--. |
| 24 | 2 | Change "xenogenic" to --xenogeneic--. |
| 24 | 32 | Change "glenipin," to --genipin,--. |
| 24 | 43 | Change "xenogenic" to --xenogeneic--. |
| 27 | 17 | Change "agents" to --agent--. |
| 29 | 10 | Change "form" to --from--. |
| 30 | 8 | Change "xeno geneic" to --xenogeneic--. |
| 31 | 28 | After "that" delete "the". |
| 35 | 56 | Change "no" to --not--. |
| 38 | 2 | In Claim 13, change "xenogenic" to --xenogeneic--. |